(12) United States Patent
Deng et al.

(10) Patent No.: US 6,713,286 B2
(45) Date of Patent: Mar. 30, 2004

(54) COMPOSITIONS AND METHODS FOR PROTECTING ANIMALS FROM LENTIVIRUS-ASSOCIATED DISEASE SUCH AS FELINE IMMUNODEFICIENCY VIRUS

(75) Inventors: Ruitang Deng, Old Lyme, CT (US); Michael G. Sheppard, Stonington, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/738,847

(22) Filed: Dec. 15, 2000

(65) Prior Publication Data

US 2001/0010816 A1 Aug. 2, 2001

Related U.S. Application Data

(62) Division of application No. 09/378,810, filed on Aug. 23, 1999.
(60) Provisional application No. 60/097,645, filed on Aug. 24, 1998.

(51) Int. Cl.⁷ .................................................. C12P 19/34
(52) U.S. Cl. .............................. 435/91.33; 435/320.1; 435/91.4; 435/91.5; 435/440; 435/91.1
(58) Field of Search ............................ 435/91.1–91.5, 435/320.1, 440, 91.33

(56) References Cited

FOREIGN PATENT DOCUMENTS

| CA | 2004478 | 6/1990 | |
|---|---|---|---|
| CA | 2016183 | 11/1990 | |
| EP | 1074625 | 7/2001 | ........... C12N/15/49 |
| JP | 4126085 | 4/1992 | ........... C12N/15/49 |
| WO | 9105864 | 5/1991 | |
| WO | 9215684 | 12/1992 | |
| WO | WO 94/17825 | * 12/1993 | |
| WO | 9505460 | 2/1995 | ........... C12N/15/10 |
| WO | 9640953 | 12/1996 | ........... C12N/15/85 |
| WO | WO 97/32983 | * 3/1997 | |
| WO | 9732983 | 9/1997 | ........... C12N/15/49 |
| WO | 9839451 | 9/1998 | ........... C12N/15/49 |
| WO | 9840493 | 9/1998 | ........... C12N/15/49 |
| WO | 9840493 | 12/1998 | |
| WO | 9936511 | 7/1999 | ........... C12N/15/00 |

OTHER PUBLICATIONS

La Ivanoff et al., AIDS Research and Human Retroviruses, "Alteration of HIV–1 Infectivity and Neutralization by a Single Amino Acid Replacement in the V3 Loop Domain," 1991, vol. 7, No. 7, pp. 595–603.*

S–J Lee et al., AIDS Research and Human Retroviruses, "Role of the Carboxy–Terminal Portion of the HIV–1 Transmembrane Protein in Viral Transmission and Cytopathogenicity," 1989, vol. 5, No. 4, pp. 441–449.*

Ag Fisher et al., Nature, "A molecular clone of HTLV–III with biological activity," Jul. 1985, vol. 316, pp. 262–265.*

Database EMBL Online, Mar. 16, 1992, MBI accession No. X57002, XP002184020.

Mettucci, et al. J. of Virology, Vo. 71, No. 11, pp. 8368–7376, Nov. 1997.

Hosie, et al., J. of Virology, vol 74, No. 20, pp. 9403–9411 Oct. 2000.

Elyer, et al., Vaccine., vol. 15, No. 15, pp. 1437–1444, (1997).

Hosie, et al., J. of Virology, vol. 72, No. 9, pp. 7310–7319, Sep. 1998.

Sodora, et al. Aides Research & Human Retrovirsu, vol. 11, No. 4, pp. 531–533, Analysis of Feline.

Database EMBL Online, Talbott, et al., Proc. Natl. Acad. Sci, vol. 86, 81/1989, pp. 5743–5747 XP002034203.

Kiyomasu, et al., J. of Virology vol. 65, No. 8, Aug. 1991,pp. 4539–4542.

Japan Patent Abstract, vol. 16, No. 387 (C–0975), Aug. 18, 1992.

Database EMBL Online, Olmsted, et al., Proc. Natl. Acad. Sci, vol 86, No. 7 Apr. 1989, pp. 2448–2452 XP000001158.

Database EMBL "Online" Dec. 20, 1990, retrieved from EBI, accession #M25381/M25729, XP002184019.

Database EMBL Online, Omsted, et al., Proc. Natl. Acad. Sci., vol. 86, Oct. 1989, pp. 8088–8092, XP002067357.

Phillips T. R., et al., J. of Virology, vol. 64, No. 10, pp. 4605–4613, Oct. 1, 1990.

Leamer, et al. *Increased mutation frequency of feline immunodeficiency virus lacking functional deoxyuridine–triphosphatase,* Proc. Natl. Acad. Sci., 92. pp. 7480–7484 (1995).

* cited by examiner

Primary Examiner—Dave T. Nguyen
Assistant Examiner—J. Eric Angell
(74) Attorney, Agent, or Firm—Peter C. Richardson; Gregg C. Benson; Martha G. Munchhof

(57) ABSTRACT

The present invention is directed to a novel strain of feline immunodeficiency virus, designated herein as FIV-141, and to attenuated forms of the virus produced by mutating specific regions of the viral genome. The virus and mutated forms of the virus may be used to induce the production of antibodies to FIV-141, and in vaccines designed to protect cats from FIV.

3 Claims, 11 Drawing Sheets

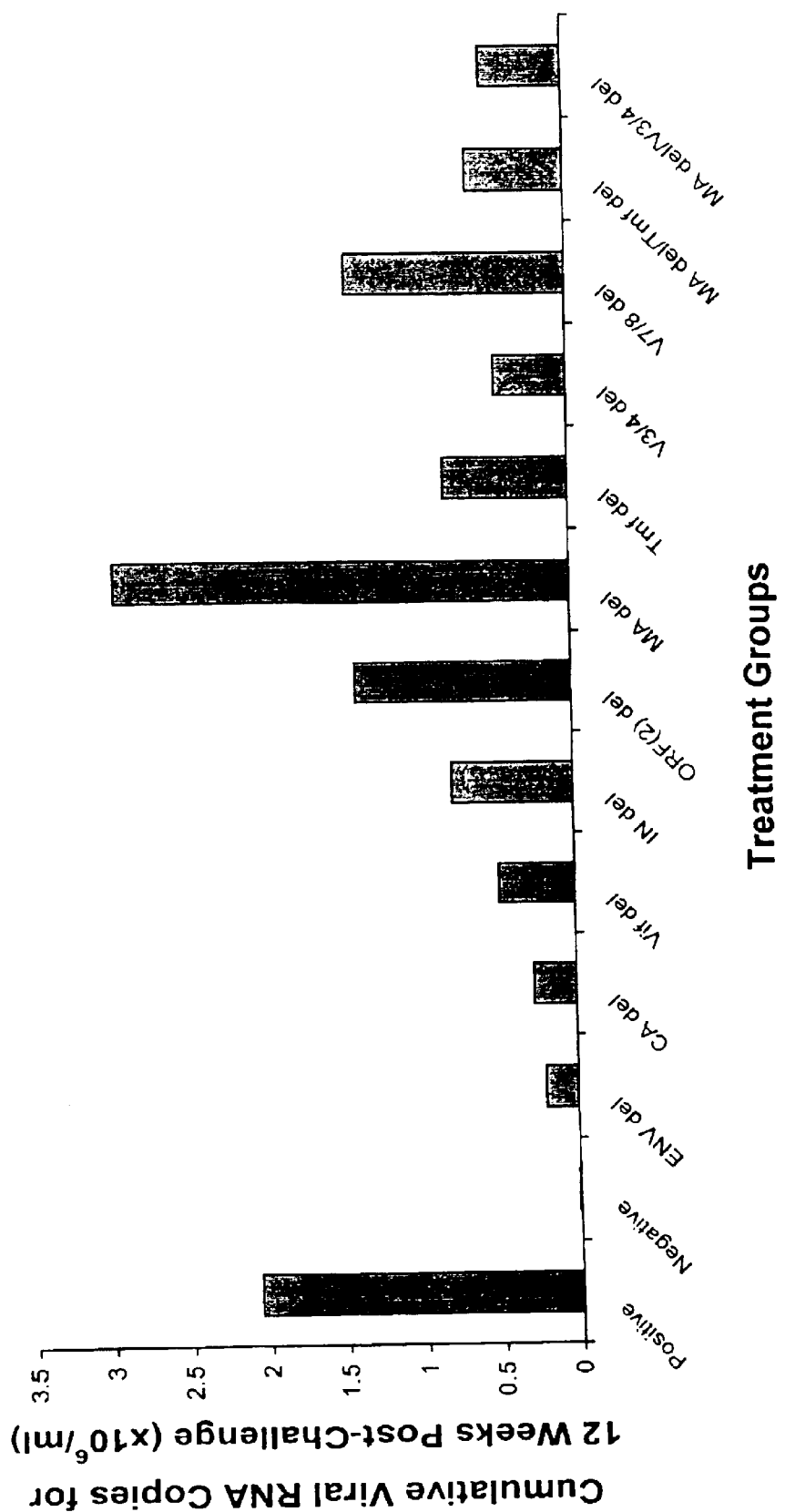

SEQUENCE LISTING

<160> NUMBER OF SEQ ID NOS: 59

<210> SEQ ID NO 1
<211> LENGTH: 9464
<212> TYPE: DNA
<213> ORGANISM: Feline immunodeficiency virus

<400> SEQUENCE: 1

```
tgggaagatt attgggatcc tgaagaaata gaaaaaatgc taatggactg aggacgtaca      60
taaacaagtg acagatggaa acagctgaat atgactcaat gctagcagct gcttaaccgc     120
aaaaccacat cctatgtaaa gcttgccgat gacgtgtatc ttgctccatt ataagagtat     180
ataaccagtg ttttgtaaaa gcttcgagga gtctctctgt tgagggcttt cgagttctcc     240
cttgaggctc ccacagatac aataaaaaac tgagctttga gattgaaccc tgtcttgtat     300
ctgtgtaatt tctcttacct gcgaatccct ggagtccggg ccagggacct cgcagttggc     360
gcccgaacag ggacttgaaa aggagtgatt agggaagtga agctagagca atagaaagct     420
gtcaagcaga actcctgcag gccttgtatg gggagcagtt gcagacgctg ctggcagtga     480
gtatctctag tggagcggac ctgagctctg gattaagtca ctgctcacag gcctagataa     540
agattatctg gtgactcttc gcggatcgtc aaaccagggg attcgtcggg ggacagccaa     600
caaggtagga gagattctac agcaacatgg ggaatggaca ggggcgagac tggaaaatgg     660
ccattaagag atgtagtaat gttgctgtag gggtagggag caggagtaaa aaatttggag     720
aaggaaattt tagatgggcc ataaggatgg ctaatgtaac tacaggacga gaacctggtg     780
atataccaga gactttagaa cagctaagat caatcatttg tgacttacaa gacagaagag     840
aacaatatgg atctagtaaa gaaattgaca tggcaattac cactttaaaa gtttttgcag     900
tggcaggaat tctaaatatg actgtaacta ctgccacagc agctgaaaat atgtatgctc     960
agatgggatt agacaccaga ccatctataa agaaagtgg gggaaaagaa gaaggacctc    1020
cacaggctta tcctattcaa acagtaaatg gagcaccaca gtatgtagcc cttgatccaa    1080
aaatggtgtc tattttatg gagaaggcaa gagaggggct aggaggtgaa gaagtccaac    1140
tgtggtttac agccttttca gctaatttaa catcaactga tatggctaca ttaattatgt    1200
ccgcacctgg ctgtgcagca gataaagaaa tcctagatga aacactgaaa cagatgacag    1260
ctgagtatga tcgtacccat cctcctgatg gcctagacc gctgccctat ttcactgccg    1320
cagagatcat ggggatagga ttgactcaag aacaacaagc agaacccagg tttgcccag    1380
ccagaatgca gtgtagagca tggtatcttg aagcattagg aaagctagcg gccataaaag    1440
ccaaatctcc ccgagcagta caattgaagc agggagctaa agaggactat tcctcattca    1500
tagatagact atttgctcaa atagatcaag agcagaacac agctgaggta aagctgtatt    1560
```

```
taaaacaatc tttgagcata gcaaatgcta atccagattg taagagagcg atgagtcatc   1620
ttaaaccaga aagtacttta gaagagaaac tgagagcctg ccaggaaata ggatcgccag   1680
gatacaaaat gcaactattg gcagaggctc ttactagggt gcaaacagtt caagcaaaag   1740
gaccaaggcc agtatgtttc aattgtaaaa aaccaggaca cctggccaga caatgtagac   1800
aagcaaagag atgtaataaa tgtggaaaac ctggtcactt agctgctaac tgttggcaag   1860
gaggtaaaaa gtccccggga aacggggcga tggggcgagc tgcagcccca gtaaatcaag   1920
tgcagcaagt gataccatct gcaccccgg tagaggagaa attgttagat atgtaaacta   1980
taataaagtg ggtaccacca caactttaga aaaagacct gaaatacaaa tattcgtaaa   2040
tgggtatcct ataaaatttt tattagatac aggagcagat ataacaattt taaacagaaa   2100
agactttcag atagggaatt ctatagaaaa tgggaaacag aatatgattg gagtaggagg   2160
cggaaagaga ggaacaaatt atatcaatgt gcatttagaa attagagatg aaaattataa   2220
gacacagtgt atatttggaa atgtgtgtgt cttggaggat aattcattaa tacaaccatt   2280
attgggaaga gataacatga ttaagttcaa cataaggttg gtaatggctc aaatttcaga   2340
gaaaattcca atagtaaaag taagaatgaa agaccctact caagggcctc aggtaaaaca   2400
atggccatta tcaaatgaga aaattgaagc tctaactgac atagtaaaca ggttagaaca   2460
agagggaaag gtaaaagag ctgatccaaa taatccttgg aacactcccg tatttgcaat   2520
caagaaaaag aatggtaaat ggagaatgct catagatttt agggtcctaa ataaattaac   2580
agacaaaggg gcagaagttc agttaggact ccctcatcct gctggattac aattgaaaaa   2640
acaagtaact gtattggaca taggggacgc atatttact attcctctag atccagatta   2700
tgctccttat actgcattta cactacctag aaaaaacaat gcaggaccag ggaggagata   2760
catatggtgt agtttaccac aagggtgggt cttgagtcca ttgatatatc agagtacctt   2820
agacaatata ctccaacctt ttattaaaca gaatcctgag ttagatattt atcaatatat   2880
ggatgatatc tataggat caaatttaag taaaaggaa cataaactaa aagtagaaga   2940
attaagaaaa ttgttattat ggtggggatt tgaaaccccg gaagataaat tacaagaaga   3000 gccccctat aagtggatgg ctatgaatt acatccatta acgtggtcaa tacagcaaaa   3060
gcaattagaa attccagaga gacccacatt aaatgaatta cagaagttag caggtaagat   3120
taactgggct agtcaaacca ttccagactt gagcataaaa gaactaacta atatgatgag   3180
aggagatcaa aagttagact caataagaga atggacgaca gaggccaaga atgaagtgga   3240
gaaagctaag agagcaattg agacacaggc acagctagga tattatgatc ctaatcgaga   3300
attatatgct aaattaagtc ttgtgggacc acatcaacta agctatcagg tgtatcataa   3360
aaacccagaa cagatattat ggtatgggaa aatgaatagg cagaagaaaa aagcagaaaa   3420
tacttgtgat atagctctaa gggcatgtta caaataaga gaagaatcca ttataagaat   3480
aggaaaagaa ccagtatatg aaatacctac atccagagaa gcttgggaat caaatctaat   3540
tagatctcca tatcttaagg cctcaccacc tgaggtggaa tttatacatg ctgccttaaa   3600
tataaaaaga gctctaagca tgatacaaga tgcccctata ttgggagcag aaacatggta   3660
catagatggg ggaagaaaac aaggaaaagc agcaagagca gcttattgga cagatacggg   3720
cagatggcag gtaatggaaa tagaaggaag taatcaaaaa gcagaagtac aagctttatt   3780
attggcccta caggcaggac cagaggaaat gaatattata acagattcac aatatattgt   3840
gaatattatt aatcaacaac cagatttgat ggaaggaatt tggcaagaag tcttagaaga   3900
```

-continued

```
aatggaaaag aaagtagcaa tctttataga ttgggtacct ggacataaag gtattccagg    3960
aaataaagag gtagatgaac tttgtcaaac gatgatggtt atagaaggtg aaggaatatt    4020
agataaaaga tcagaagatg caggatatga tttattagct gcacaagaaa tacatctctt    4080
gcctggggag gtaagagtag taccaacaag aacaaagata atgttaccta aggatattg    4140
gggattaata atgggaaaaa gttcaatggg aagcaaagga ttagatgtat taggaggagt    4200
tatagatgaa ggatatagag gagaattagg ggtgataatg attaacctat ctaaaaaatc    4260
aataacatta tcagaaaaac aaaaagtagc acaattaata atattacctt gtaaacatga    4320
aagcttacaa caaggagaaa taataatgga ttcagaaaga ggaagaaagg gatttgggtc    4380
aactggagtc ttttcttcat gggtggacag aattgaggaa gcagaattaa atcatgaaaa    4440
atttcactca gacccacaat acttaagaac agaatttaat ctacccagaa tagtagcaga    4500
ggaaataaaa agaaaatgtc ccttatgtag aatcagaggg gaacaagtag ggggacaatt    4560
aaagattgga cctggcatat ggcaaatgga ctgtacacac tttaatggaa aaataattat    4620
tgtcgcagtg catgtggaat caggcttatt atgggcacag gtaattccac aggagactgc    4680
agattgtaca gttaaagctc tcatgcaact tatcagtgct cataatgtta cagaactaca    4740
aacagataat ggaccaaatt ttaaaaatca gaaaatggaa ggactactaa attatatggg    4800
cataaaacac aaattaggta taccaggtaa cccacaatca caagcattag tagaaaatgc    4860
taaccacaca ttaaaatctt ggattcaaaa atttctctca gaaacttctt ctttggacaa    4920
cgcattggcc ctagccttat actgcctcaa ttttaaacaa aggggtagac tagggagaat    4980
ggctccttat gaattataca tacaacagga atcattaaga atacaagact atttttcaca    5040
aattccacaa aaattaatga tgcaatgggt gtattataaa gatcagaaag ataaaaagtg    5100
gaagggacca atgagagtag aatattgggg acaaggatca gtattattaa gaatgaaga    5160
gaagggatat tttcttgtac ctaggagaca cataagaaga gtcccagaac cctgcactct    5220
tcctgaaggg gatgagtgac gaagattggc aggtaagtag aagactcttt gcagttctcc    5280
aaggaggagt aaatagtgcc atgttataca tatcgaattt acctgaaaca gaacaggcac    5340
aatataaaaa ggactttaag aaaaggctct tagaaaagga gactggattc atctatagat    5400
taagaaaagc tgaaggaata aggtggagct ttcatacgcg tgattattat ataggatatg    5460
taagagagat ggtggctggg tctagcctac aaaatagttt aagattgtat gtttatataa    5520
gcaatccatt gtggcatcag tcataccgtc ctggcctgac aaattttaat acagagtggc    5580
cttttgtaaa tatgtggata aagacaggat ttatgtggga tgatattgaa agccaaaata    5640
tttgcaaagg aggagagatc tcacatggat gggggacctgg aatggtggga attgtgataa    5700
aagcatttag ctgtggagaa aggaagatac aaattactcc tgtcatgatt ataagaggtg    5760
agatagaccc acagaaatgg tgtggagatt gttggaatct gatgtgtctt aaatattcac    5820
ttccaaatac attgcagagg cttgctatgc tggcgtgtgg caaagaggct aaagaatgga    5880
gaggctgttg taatcagcgt tttgtttctc ctttcagaac accctgtgat ctagaggtcg    5940
tccagaacaa gcctaaaagg aatttattgt ggacgggaga attatgaatg gaagaaataa    6000
tcccactgtt taataaggtt acagaaaagt tagatagaga agcagctatt agattgttta    6060
ttttagctta tcaggtagac agatgcagat ttattagaat tttacaatta ttactttgga    6120
gagatagatt taagtcaatc aattctaaat attgtttatg ctggctgtgc tgcaagtctg    6180
cttattggcg cttgcaatct acattatcca taaatactgc ctagaaatat ttctttaat    6240
atttcatctg cagatataaa catggcagag ggaggattta ctcaaaatca acaatggata    6300
```

```
gggccagaag aagctgaaga attgttagat tttgatatag ctgtacaaat gaatgaagaa    6360
ggtccattaa acccaggagt aaacccattt agggtaccag gaattacctc tcaagaaaag    6420
gatgattatt gtcagatttt acaaccaaaa ctacaagaat taaagaatga aatcaaagag    6480
gtaaaacttg acgaaaacaa tgcaggtaag tttagaaagg caagatattt aagatattct    6540
gatgagagtg tactaactat agtctattta ctaacaggat atttgagata tttaataagc    6600
catagaaact taggatcttt aagacatgat atagatatag aagcaccaca acaagagcac    6660
tataatgata agaaaaggg tactacttta aatataaagt atgggagaag atgttgtatt    6720
agcacattac ttctatattt aatcctcttc tcagggatag gaatttggct tggaaccaaa    6780
gcacaagtag tgtggagact ccctccttta gtagtgccag tagatgagac agaaataata    6840
ttttgggatt gttgggcgcc agaggaacca gcctgtcaag attttctggg aacaatgata    6900
catttaaaag caaatgttaa tataagtata caagaaggac ctacattggg aaattgggca    6960
agggaaattt ggtctacatt atttaaaaaa gctacaaggc aatgcagaag gggaaggata    7020
tggaagaaat ggaatgagac tataacagga cctaaaggat gtgcaaataa tacctgttat    7080
aatatttcag tagtggtacc tgattatcaa tgttatgtag acagagtaga tacatggctg    7140
caaggaaaag ttaatatctc actatgtttg acaggaggaa agatgctata taataaaaat    7200
acaaaacaat taagttactg tacagatcca ttacaaatac cattaattaa ttacacattt    7260
ggacctaacc aaacttgtat gtggaacaca tctttaatca aagaccctga gataccgaaa    7320
tgtggatggt ggaaccaggc agcctattat aataattgta atgggaaga agctaatgtg    7380 acatttcaat gtcaaagatc acaaagtcta ccaggatcat gggttaggag aatctcttca    7440
tggagacaaa gaaacagatg ggagtggagg ccagactttg aaagtgagaa agtaaaaata    7500
tcattacaat gtaatagtac aaaaaattta acttttgcaa tgagaagttc aagtgattat    7560
tatgatgtac aaggagcatg gatagaattt ggatgttata gaaataaatc aagaacccat    7620
acgggagcaa gatttagaat aagatgtaaa tggaatgaag aaagaatct atctctcatt    7680 gatacatgtg ggactacttc aaatgtgaca ggagccaacc ctgtagattg tactatgaaa    7740
acaagcacta tgtacaattg ttccttacaa gatagtttca ctatgaaaat agaggacctt    7800
attgtacaat ttaatatgac aaaagcagtg gaaatgtata atattgctgg gaattggtct    7860 tgtcacatctg atttaccaac agggtgggga tatatgaaat gtaattgtac aaatgccact    7920
gatggggaga ataaaatgaa atgccctagg aatcagggta ttttaagaaa ctggtacaat    7980
ccagttgcag gactaagaca agctcttatg aagtatcaag tagtaaaaca accagaaatat    8040 ttggtggtac cggaagaagt tatgagggtat aaaggtaaac aaaaaggc cgctattcat    8100 attatgttag cccttgctac ggtgttatct atagctggag caggaaccgg tgccactgct    8160
attgggatgg tgcacacta tcagcaagtt ttggctaccc atcagcaggc attggacaaa    8220
ataactgagg cactgaaaat aaacaactta aggttaatca ctttagaaca tcaagtatta    8280
gtgatagggt taaagtaga ggctatagaa aaattcctat atacagcttt tgctatgcaa    8340
gaattaggat gtaatcagaa tcaattcttt tgtaagattc ccctcaatct gtggacaatg    8400
tataacatga ctataaatca tacactatgg aatcatggaa atataacttt gggagaatgg    8460
tataatcaaa caaaaagttt acaagaaaaa ttttatgaga taattatgga tatagaacaa    8520
aataatgtac aagggaaaaa tggaatacaa caattacaaa aatgggaaaa ttgggtggga    8580
tggataggca aaatccctca atatttaaaa ggacttcttg gtagtgtgtt gggaatagga    8640
```

```
ctaggaatct tactactact tatatgcttg cctacattag tagattgtat aagaaactgt   8700
actaataaaa tattgggata tacagttatt gcaatgcctg aaatagatga tgaggaagta   8760
cacccatcag tggaattgag gagaaatggc aggcaatgtg gcatatctga aaagaggag    8820 gaatgatgga gcatttcaga cctgtagaat acaggagtaa tgctgagctg agttcttccc   8880
tttgaggagg atgtgtcata tgaatccatt tcaaatcaaa aataacagta aaatctatat   8940
tgtaaggcaa acgaaaaaga caacgcagaa gaagaaagaa gaaggccttc aaaaaattga   9000
tgctggattt agaggctcga tttaaagcgt tgtttgaaac accttcagct acagaatata   9060
ctgcagacga gacagaagaa gagactcttg aaaaagaaaa aagggtggac tgggaagatt   9120
attgggatcc tgaagaaata gaaaaaatgc taatggactg aggacgtaca taaacaagtg   9180
acagatggaa acagctgaat atgactcaat gctagcagct gcttaaccgc aaaaccacat   9240
cctatgtaaa gcttgccgat gacgtgtatc ttgctccatt ataagagtat ataaccagtg   9300
ttttgtaaaa gcttcgagga gtctctctgt tgagggcttt cgagttctcc cttgaggctc   9360
ccacagatac aataaaaaac tgagctttga gattgaaccc tgtcttgtat ctgtgtaatt   9420
tctcttacct gcgaatccct ggagtccggg ccagggacct cgca                    9464
```

<210> SEQ ID NO 2
<211> LENGTH: 30
<212> TYPE: DNA
<213> ORGANISM: Feline immunodeficiency virus

<400> SEQUENCE: 2

```
ccgcaaaacc acatcctatg taaagcttgc                                       30
```

<210> SEQ ID NO 3
<211> LENGTH: 30
<212> TYPE: DNA
<213> ORGANISM: Feline immunodeficiency virus

<400> SEQUENCE: 3

```
cgcccctgtc cattccccat gttgctgtag                                       30
```

<210> SEQ ID NO 4
<211> LENGTH: 30
<212> TYPE: DNA
<213> ORGANISM: Feline immunodeficiency virus

<400> SEQUENCE: 4

```
ttactgtttg aataggatat gcctgtggag                                       30
```

<210> SEQ ID NO 5
<211> LENGTH: 30
<212> TYPE: DNA
<213> ORGANISM: Feline immunodeficiency virus

<400> SEQUENCE: 5

```
gcaatgtggc atgtctgaaa agaggagga                                        30
```

<210> SEQ ID NO 6
<211> LENGTH: 34
<212> TYPE: DNA
<213> ORGANISM: Feline immunodeficiency virus

<400> SEQUENCE: 6

```
tcttcccttt gaggaagata tgtcatatga atcc                                  34
```

```
<210> SEQ ID NO 7
<211> LENGTH: 26
<212> TYPE: DNA
<213> ORGANISM: Feline immunodeficiency virus

<400> SEQUENCE: 7
tctgtgggag cctcaaggga gaactc                                          26

<210> SEQ ID NO 8
<211> LENGTH: 30
<212> TYPE: DNA
<213> ORGANISM: Feline immunodeficiency virus

<400> SEQUENCE: 8
acaaacagat aatggaccaa attttaaaaa                                      30

<210> SEQ ID NO 9
<211> LENGTH: 28
<212> TYPE: DNA
<213> ORGANISM: Feline immunodeficiency virus

<400> SEQUENCE: 9
tttcaatatc atcccacata aatcctgt                                        28

<210> SEQ ID NO 10
<211> LENGTH: 30
<212> TYPE: DNA
<213> ORGANISM: Feline immunodeficiency virus

<400> SEQUENCE: 10
ttaaaggatg aagagaaggg atattttctt                                      30

<210> SEQ ID NO 11
<211> LENGTH: 30
<212> TYPE: DNA
<213> ORGANISM: Feline immunodeficiency virus

<400> SEQUENCE: 11
tgggaagatt attgggatcc tgaagaaata                                      30

<210> SEQ ID NO 12
<211> LENGTH: 40
<212> TYPE: DNA
<213> ORGANISM: Feline immunodeficiency virus

<400> SEQUENCE: 12
catatcctat ataataatca cgcgtatgaa agctccacct                           40

<210> SEQ ID NO 13
<211> LENGTH: 24
<212> TYPE: DNA
<213> ORGANISM: Feline immunodeficiency virus

<400> SEQUENCE: 13
tgcgaggtcc ctggcccgga ctcc                                            24

<210> SEQ ID NO 14
<211> LENGTH: 40
<212> TYPE: DNA
<213> ORGANISM: Feline immunodeficiency virus

<400> SEQUENCE: 14
aggtggagct ttcatacgcg tgattattat ataggatatg                           40
```

```
<210> SEQ ID NO 15
<211> LENGTH: 29
<212> TYPE: DNA
<213> ORGANISM: Feline immunodeficiency virus

<400> SEQUENCE: 15
ctccagggat tcgcaggtaa gagaaatta                                    29

<210> SEQ ID NO 16
<211> LENGTH: 49
<212> TYPE: DNA
<213> ORGANISM: Feline immunodeficiency virus

<400> SEQUENCE: 16
ttacaagaat tcaactgcag tgggaagatt attgggatcc tgaagaaat              49

<210> SEQ ID NO 17
<211> LENGTH: 42
<212> TYPE: DNA
<213> ORGANISM: Feline immunodeficiency virus

<400> SEQUENCE: 17
ttcaaggagc tcttttgtcg acaactgcga ggtccctggc cc                     42

<210> SEQ ID NO 18
<211> LENGTH: 53
<212> TYPE: DNA
<213> ORGANISM: Feline immunodeficiency virus

<400> SEQUENCE: 18
gattcgtcgg gggacagcca acaaggtagg agagattcta cagcaacatg ggg         53

<210> SEQ ID NO 19
<211> LENGTH: 42
<212> TYPE: DNA
<213> ORGANISM: Feline immunodeficiency virus

<400> SEQUENCE: 19
tcaatatatg gatgatatct ataggatc aaatttaagt aa                       42

<210> SEQ ID NO 20
<211> LENGTH: 58
<212> TYPE: DNA
<213> ORGANISM: Feline immunodeficiency virus

<400> SEQUENCE: 20
gtgatatagc tctaagggca tgttacaaaa taagagaaga atccattata agaatagg    58

<210> SEQ ID NO 21
<211> LENGTH: 46
<212> TYPE: DNA
<213> ORGANISM: Feline immunodeficiency virus

<400> SEQUENCE: 21
cgggcagatg gcaggtaatg gaaatagaag gaagtaatca aaaagc                 46

<210> SEQ ID NO 22
<211> LENGTH: 44
<212> TYPE: DNA
<213> ORGANISM: Feline immunodeficiency virus

<400> SEQUENCE: 22
agaaagggat ttgggtcaac tggagtcttt tcttcatggg tgga                   44
```

<210> SEQ ID NO 23
<211> LENGTH: 51
<212> TYPE: DNA
<213> ORGANISM: Feline immunodeficiency virus

<400> SEQUENCE: 23
gggggacaat taaagattgg acctggcata tggcaaatgg actgtacaca c        51

<210> SEQ ID NO 24
<211> LENGTH: 49
<212> TYPE: DNA
<213> ORGANISM: Feline immunodeficiency virus

<400> SEQUENCE: 24
ggctccttat gaattataca tacaacagga atcattaaga atacaagac             49

<210> SEQ ID NO 25
<211> LENGTH: 36
<212> TYPE: DNA
<213> ORGANISM: Feline immunodeficiency virus

<400> SEQUENCE: 25
caaaatagtt taagattgta tgtttatata agcaat                          36

<210> SEQ ID NO 26
<211> LENGTH: 40
<212> TYPE: DNA
<213> ORGANISM: Feline immunodeficiency virus

<400> SEQUENCE: 26
cagaaaagtt agatagagaa gcagctatta gattgtttat                      40

<210> SEQ ID NO 27
<211> LENGTH: 40
<212> TYPE: DNA
<213> ORGANISM: Feline immunodeficiency virus

<400> SEQUENCE: 27
taaaagcaaa tgttaatata agtatacaag aaggacctac                      40

<210> SEQ ID NO 28
<211> LENGTH: 40
<212> TYPE: DNA
<213> ORGANISM: Feline immunodeficiency virus

<400> SEQUENCE: 28
aaaagctaca aggcaatgca gaaggggaag gatatggaag                      40

<210> SEQ ID NO 29
<211> LENGTH: 44
<212> TYPE: DNA
<213> ORGANISM: Feline immunodeficiency virus

<400> SEQUENCE: 29 agaggaccttt attgtacaat ttaatatgac aaaagcagtg gaaa                44

<210> SEQ ID NO 30
<211> LENGTH: 40
<212> TYPE: DNA
<213> ORGANISM: Feline immunodeficiency virus

<400> SEQUENCE: 30

```
ccctcaatct gtggacaatg tataacatga ctataaatca            40
```

<210> SEQ ID NO 31
<211> LENGTH: 40
<212> TYPE: DNA
<213> ORGANISM: Feline immunodeficiency virus

<400> SEQUENCE: 31

```
gacaacgcag aagaagaaag aagaaggcct tcaaaaaatt           40
```

<210> SEQ ID NO 32
<211> LENGTH: 50
<212> TYPE: DNA
<213> ORGANISM: Feline immunodeficiency virus

<400> SEQUENCE: 32

```
agtaaagaaa ttgacatggc gattactagt ttaaaagttt ttgcagtggc   50
```

<210> SEQ ID NO 33
<211> LENGTH: 47
<212> TYPE: DNA
<213> ORGANISM: Feline immunodeficiency virus

<400> SEQUENCE: 33

```
ccatctataa aagaaagtgg gactagtgaa gaaggacctc cacaggc    47
```

<210> SEQ ID NO 34
<211> LENGTH: 51
<212> TYPE: DNA
<213> ORGANISM: Feline immunodeficiency virus

<400> SEQUENCE: 34

```
attcaaacag taaatggagc aactagttat gtagcccttg atccaaaaat g   51
```

<210> SEQ ID NO 35
<211> LENGTH: 51
<212> TYPE: DNA
<213> ORGANISM: Feline immunodeficiency virus

<400> SEQUENCE: 35

```
acagcctttt cagctaattt aactagtact gatatggcta cattaattat g   51
```

<210> SEQ ID NO 36
<211> LENGTH: 50
<212> TYPE: DNA
<213> ORGANISM: Feline immunodeficiency virus

<400> SEQUENCE: 36

```
actatagtct atttactaac tggttacctg agatatttaa taagccatag   50
```

<210> SEQ ID NO 37
<211> LENGTH: 54
<212> TYPE: DNA
<213> ORGANISM: Feline immunodeficiency virus

<400> SEQUENCE: 37

```
tacttatatg cttgcctaca ttgggttacc gtataagaaa ctgtactaat aaaa   54
```

<210> SEQ ID NO 38
<211> LENGTH: 54
<212> TYPE: DNA
<213> ORGANISM: Feline immunodeficiency virus

<400> SEQUENCE: 38

```
gaggtataaa ggtaaacaaa aaactagtgc cattcatatt atgttagccc ttgc        54
```

<210> SEQ ID NO 39
<211> LENGTH: 58
<212> TYPE: DNA
<213> ORGANISM: Feline immunodeficiency virus

<400> SEQUENCE: 39

```
actaactata gtctatttac taacaactag tttgagatat ttaataagcc atagaaac    58
```

<210> SEQ ID NO 40
<211> LENGTH: 62
<212> TYPE: DNA
<213> ORGANISM: Feline immunodeficiency virus

<400> SEQUENCE: 40

```
ataccgaaat gtggatggtg gaatcaggca tgctattata ataattgtaa atgggaagaa  60
gc                                                                62
```

<210> SEQ ID NO 41
<211> LENGTH: 58
<212> TYPE: DNA
<213> ORGANISM: Feline immunodeficiency virus

<400> SEQUENCE: 41

```
gcactatgta caattgttcc ttacaggcat gcttcactat gaaatagag gaccttat     58
```

<210> SEQ ID NO 42
<211> LENGTH: 56
<212> TYPE: DNA
<213> ORGANISM: Feline immunodeficiency virus

<400> SEQUENCE: 42

```
gaatcaattc ttttgtaaga tcgcatgcaa tctgtggaca atgtataaca tgacta      56
```

<210> SEQ ID NO 43
<211> LENGTH: 61
<212> TYPE: DNA
<213> ORGANISM: Feline immunodeficiency virus

<400> SEQUENCE: 43

```
gggaaaattg ggtgggatgg ataggtaaga tcgcatgcta tttaaaagga cttcttggta  60
g                                                                 61
```

<210> SEQ ID NO 44
<211> LENGTH: 40
<212> TYPE: DNA
<213> ORGANISM: Feline immunodeficiency virus

<400> SEQUENCE: 44

```
ggaagaagtt atgaggtata ccggtaaaca aaaaagggcc                       40
```

<210> SEQ ID NO 45
<211> LENGTH: 62
<212> TYPE: DNA
<213> ORGANISM: Feline immunodeficiency virus

<400> SEQUENCE: 45

```
ctacttatat gcttgcctac attggtcgac tgatagtgaa actgtactaa taaatattg   60
gg                                                                62
```

<210> SEQ ID NO 46
<211> LENGTH: 56
<212> TYPE: DNA
<213> ORGANISM: Feline immunodeficiency virus

<400> SEQUENCE: 46
gatggttata gaaggtgaag gaattactag taaaagatca gaagatgcag gatatg       56

<210> SEQ ID NO 47
<211> LENGTH: 59
<212> TYPE: DNA
<213> ORGANISM: Feline immunodeficiency virus

<400> SEQUENCE: 47
gaaataataa tggattcaga aagaggaact agtggatttg ggtcaactgg agtcttttc    59

<210> SEQ ID NO 48
<211> LENGTH: 57
<212> TYPE: DNA
<213> ORGANISM: Feline immunodeficiency virus

<400> SEQUENCE: 48
cttcatgggt ggacagaatt gaaactagtg tattaaatca tgaaaaattt cactcag      57

<210> SEQ ID NO 49
<211> LENGTH: 59
<212> TYPE: DNA
<213> ORGANISM: Feline immunodeficiency virus

<400> SEQUENCE: 49
gcaatgggtg tattataaag atcagactag taaaaagtgg aagggaccaa tgagagtag    59

<210> SEQ ID NO 50
<211> LENGTH: 57
<212> TYPE: DNA
<213> ORGANISM: Feline immunodeficiency virus

<400> SEQUENCE: 50
agaagactct ttgcagttct ccaatgaacg cgttagagtg ccatgttata catatcg      57

<210> SEQ ID NO 51
<211> LENGTH: 44
<212> TYPE: DNA
<213> ORGANISM: Feline immunodeficiency virus

<400> SEQUENCE: 51
cgtgtggcaa agaggctaaa acgcgtagag gctgttgtaa tcag                    44

<210> SEQ ID NO 52
<211> LENGTH: 56
<212> TYPE: DNA
<213> ORGANISM: Feline immunodeficiency virus

<400> SEQUENCE: 52
gtggacggga gaattatgaa cgcgtgaact aatcccactg tttaataagg ttacag       56

<210> SEQ ID NO 53
<211> LENGTH: 55
<212> TYPE: DNA
<213> ORGANISM: Feline immunodeficiency virus

<400> SEQUENCE: 53
ctacattatc cataaatact gcctagacgc gtttctttta atatttcatc tgcag        55

```
<210> SEQ ID NO 54
<211> LENGTH: 54
<212> TYPE: DNA
<213> ORGANISM: Feline immunodeficiency virus

<400> SEQUENCE: 54
ggcatatctg aaaaagagga ggaatgaact agtatatcag acctgtagaa taca          54

<210> SEQ ID NO 55
<211> LENGTH: 59
<212> TYPE: DNA
<213> ORGANISM: Feline immunodeficiency virus

<400> SEQUENCE: 55
gaggaggatg tgtcatatga atcaaatact agtcaaaaat aacagtaaaa tctatattg     59

<210> SEQ ID NO 56
<211> LENGTH: 22
<212> TYPE: DNA
<213> ORGANISM: Feline immunodeficiency virus

<400> SEQUENCE: 56
tattatggtg gggatttgaa ac                                             22

<210> SEQ ID NO 57
<211> LENGTH: 22
<212> TYPE: DNA
<213> ORGANISM: Feline immunodeficiency virus

<400> SEQUENCE: 57
taattagatt tgattcccag gc                                             22

<210> SEQ ID NO 58
<211> LENGTH: 32
<212> TYPE: DNA
<213> ORGANISM: Feline immunodeficiency virus

<400> SEQUENCE: 58
tgtagagcat ggtatcttga agcattagga aa                                  32

<210> SEQ ID NO 59
<211> LENGTH: 35
<212> TYPE: DNA
<213> ORGANISM: Feline immunodeficiency virus

<400> SEQUENCE: 59
gttcctctct ttccgcctcc tactccaatc atatt                               35
```

US 6,713,286 B2

COMPOSITIONS AND METHODS FOR PROTECTING ANIMALS FROM LENTIVIRUS-ASSOCIATED DISEASE SUCH AS FELINE IMMUNODEFICIENCY VIRUS

This application is a division of Ser. No. 09/378,810, filed Aug. 23, 1999, which claimed the benefit of Ser. No. 60/097,645, filed Aug. 24, 1998.

FIELD OF THE INVENTION

The present invention is directed to a novel strain of feline immunodeficiency virus (FIV) and to a variety of mutated forms of this virus. Compositions and methods are disclosed that can be used in the protection of animals from lentiviral associated disease.

BACKGROUND OF THE INVENTION

Feline immunodeficiency virus (FIV) infection in cats results in a disease syndrome that is similar to that caused by human immunodeficiency virus-1 (HIV-1) infection in humans. Disease progression begins with a transient acute phase (8–10 weeks), followed by a prolonged asymptomatic phase (lasting from weeks to years) and a terminal symptomatic phase (Ishida et al., 1990, Jpn. J. Vet. Sci. 52:645–648). Viral load in plasma has been demonstrated to correlate with disease stage in infected cats and can be used to predict disease progression in accelerated FIV infection (Diehl et a., 1996, J. Virol. 70:2503–2507).

Structurally, the FIV provirus contains two long terminal repeats (LTRs), one at either end of the genome (Talbott et al., 1989, Proc. Nat'l Acad. Sci. USA 86:5743–5747). There are three large open reading frames (Gag (group antigens); Pol (polymerase); and ENV (envelope)) and three small open reading frames encoding regulatory proteins (Rev (regulator of expression of virion, a protein that binds to "RRE" elements present in all viral transcripts and promotes their translocation from the nucleus to the cytoplasm of infected host cells); Vif (virion infectivity factor); and ORF (2) (open reading frame 2)). The Gag precursor polypeptide of FIV is processed into three mature structural proteins: a matrix protein (MA), a capsid protein (CA), and a nucleocapsid protein (NC). The Pol gene encodes four enzymatic proteins: a protease (PR), a reverse transcriptase (RT), a deoxyuridine triphosphatase (DU), and an integrase (IN). Finally, the ENV precursor polypeptide is processed into two envelope proteins: a surface protein (SU) and a transmembrane (TM) protein.

There have been several attempts to develop a safe and effective vaccine to FIV. Matteucci found that cats inoculated with a conventional fixed cell vaccine were protected from challenge with homologous virus despite an apparent absence of neutralizing antibodies after vaccination. Protection was found to be short-lived and difficult to boost (Matteucci et al., 1996, J. Virol. 70:617–622; Matteucci et al., 1997, J. Virol. 71:8368–8376). These results may be contrasted with those of Verschoor, who observed no protection after the administration of a fixed cell vaccine (Verschoor et al., 1995, Vet. Immunol. Immunopathol. 46:139–149).

Another type of conventional vaccine that has been tested is comprised of whole, inactivated FIV virus. Yamamoto reported that greater than 90% of cats administered a vaccine of this type exhibited essentially complete protection against homologous challenge and slight protection against heterologous virus (Yamamoto et al., 1993, J. Virol. 67:601–605). Both humoral and cellular immunity against FIV were induced and a high level of anti-ENV, anti-core and virus neutralizing (VN) antibodies were observed in the vaccinated cats. In contrast, vaccination of cats with inactivated whole FIV incorporated into immune stimulating complexes (ISCOMS) failed to protect animals from homologous challenge (Hosie et al., 1992, Vet. Immunol. Immunopathol. 35:191–197).

Another approach to vaccine development has involved the use of subunit vaccines containing recombinant core protein, synthetic V3 peptides, and recombinant ENV protein (Elyar et al., 1997, Vaccine 15:1437–1444). Although significant levels of antibodies were induced by such vaccines, none were identified that could protect cats against homologous FIV challenge (Huisman et al., 1998, Vaccine 16:181–187; Flynn et al., 1997, J. Virol. 71:7586–7592; Tijhaar et al., 1997, Vaccine 15:587–596). The results suggest that it is likely to be difficult to obtain protective immunity against FIV using subunit type vaccines.

Recently, Cuisinier reported on tests conducted on a DNA vaccine for FIV (Cuisinier et al., 1997, Vaccine 15:1085–1094). Cats were vaccinated with a plasmid carrying FIV structural genes, including ENV and p10. Although strong humoral immune responses were observed, all cats eventually succumbed to homologous challenge.

SUMMARY OF THE INVENTION

The present invention is based, in part, upon the isolation and characterization of a new strain of feline immunodeficiency virus, designated herein as FIV-141 and deposited as ATCC No. VR-2619. The complete genomic sequence of the virus has been determined and is distinct from all other known FIV sequences. A plasmid encoding FIV-141 has been deposited as ATCC No. 203001.

A. Compositions and Methods Based upon the FIV-141 Virus

In its first aspect, the present invention is directed to a substantially purified FIV-141 virus having a genomic sequence corresponding to that of SEQ ID NO:1, to host cells infected with the virus and to progeny virus produced in the host cells. The term "substantially purified" means that FIV-141 has been separated from all other strains of virus and, particularly, from all other strains of FIV. Host cells are typically cells grown in in vitro culture. Host cells that may be used for growing virus include peripheral blood mononuclear cells (PBMCs). Progeny virus may be isolated using standard procedures as discussed below. The present invention further provides a substantially purified virus having a nucleotide sequence which is a degenerate variant of a nucleotide sequence corresponding to SEQ ID NO:1, as based on the degeneracy of the genetic code, host cells infected with such a virus, and progeny virus produced in the host cells, which are useful for all of the purposes disclosed herein for the substantially purified FIV-141 virus having a genomic sequence corresponding to that of SEQ ID NO:1, and for which all of the disclosure provided herein below is equally applicable.

The FIV-141 virus and host cells infected with the virus can be used to infect animals for the purpose of inducing the production of antibodies that react preferentially with one or more strains of FIV. "Preferential binding" of antibodies, as used herein, refers to an antibody having at least a 100-fold greater affinity for FIV than for any other virus or non-FIV protein. Antibodies may be generated in any of the animals commonly used for this purpose (such as, e.g., mice, rabbits, goats, or sheep) but, preferably, antibodies will be made in domestic cats. When virus is used to induce antibody production, it may, if desired, be inactivated prior to infection. Inactivation procedures may involve treating the virus with formalin, paraformaldehyde, phenol, lactopropionate, ultraviolet light, heat, psorlens, platinum complexes, ozone or other viricidal agents. When host cells expressing FIV-141 are used to induce antibody production, the cells may be fixed prior to infection. Typically, this will involve treating the cells with paraformaldehyde as described herein, but other methods may also be employed. Antibodies made to FIV-141 are themselves included within the scope of the invention and may be purified using techniques well known in the art (see, e.g., Harlow et al., 1988, *Antibodies: A Laboratory Manual*, Cold Spring Harbor Laboratory, N.Y.).

In another aspect, the invention is directed to a whole virus vaccine comprising inactivated FIV-141 virus, or an inactivated virus encoded by a degenerate variant of a nucleic acid molecule having a nucleotide sequence corresponding to SEQ ID NO:1. An immune response may be induced in a cat by administering this vaccine at a dosage and for a duration sufficient to induce protective immunity against subsequent infection with FIV-141. Typically, the vaccine will be administered parenterally with two or more inoculations being given at intervals of, e.g., two to eight weeks. The invention also includes a fixed cell vaccine, which is comprised of a host cell infected with the FIV-141 virus or a degenerate variant thereof. Administration of this vaccine will follow the same general procedures as used for the whole virus vaccine. Standard procedures well known in the art may be used to optimize immunization protocols.

B. Compositions and Methods Based upon FIV-141 Genomic Nucleic Acid

In another aspect, the present invention is directed to a substantially purified nucleic acid molecule (DNA or RNA) having a sequence corresponding to that of SEQ ID NO:1 or a degenerate variant thereof. As used in this context, "substantially purified" means that the desired product is essentially free from contaminating cellular components. A "substantially pure" nucleic acid will typically comprise at least 85% of a sample, with greater percentages being preferred. Contaminants may include proteins, carbohydrates or lipids. One method for determining the purity of a nucleic acid is by electrophoresing a preparation in a matrix such as polyacrylamide or agarose. Purity is evidenced by the appearance of a single band after staining. Other methods for assessing purity include chromatography and analytical centrifugation. The FIV-141 nucleic acid may be used in place of the whole virus to transfect host cells and to thereby induce the production of progeny virus or viral proteins.

The invention also encompasses methods of inducing the production of antibodies to FIV-141 by injecting nucleic acid directly into an animal or by administering host cells transfected with the nucleic acid. As with the procedures discussed above in connection with the whole virus, host cells may be fixed prior to administration. Antibodies may be substantially purified from animals and used in assays designed to detect the presence of FIV in culture medium or in a biological fluid. A "substantially purified" antibody will typically comprise at least 70% of protein in a sample, with greater percentages being preferred.

Host cells transfected with FIV-141 genomic DNA or a degenerate variant thereof may also be used in a vaccine for immunizing cats. If desired, such cells may be fixed to reduce viral infectivity, e.g., by treatment with an agent such as paraformaldehyde. Vaccines made in this manner may be used to induce an immune response in a cat. The vaccine may be administered using a standard immunization protocol optimized for the induction of protective immunity against subsequent infection with FIV-141 or, if desired, some other strain of FIV.

C. Attenuated FIV-141 Virus and Vaccines

Before a whole virus can be administered to an animal as a vaccine, it must be converted into a non-pathogenic form. As discussed above, this may be accomplished by inactivating the virus or fixing host cells. An alternative method involves introducing mutations into the virus to transform it into an attenuated form. The phrase "attenuated virus" as used in this context, refers to a virus that has substantially reduced infectivity compared to its wild type counterpart. Infectivity may be measured in PBMCs, as described in the Examples section herein below.

Thus, the invention is directed to an attenuated FIV-141 virus, or degenerate variant thereof, that exhibits significantly reduced infectivity for feline T lymphocytes relative to the wild type (i.e., non-mutated) virus. The attenuated virus is produced by mutating one or more genes in the FIV-141 genome or degenerate variant thereof selected from the group consisting of Vif, MA, ORF(2), ENV, CA, NC, SU, TMf, CT, IN, DU, V3/4, V7/8 and RRE. Appropriate mutations for each of these genes are described herein. Examples of several specific mutations that may be used in making attenuated viruses include MA del, ENV del, V3/4 del, V7/8 del, TMF del, CT del, Vif del, Vifc del, Vifn del, ORF(2) del, CA del, NC del, IN del, DU del, SU del, and RRE del. In a preferred embodiment, the attenuated virus comprises a mutation in the ENV gene. In a further preferred embodiment, the attenuated virus comprises a combination of any two or more of the aforementioned mutations. In specific though non-limiting embodiments, the attenuated virus comprises double mutations in any of the following combinations of genes: (i) MA/TMf; (ii) MA/V3/4; (iii) MA/Vif; or (iv) ENV/IN. In a preferred embodiment, the attenuated virus comprises any of the following double deletions: (i) MA del/TMf del; (ii) MA del/V3/4 del; (iii) MA del/Vif del or (iv) ENV del/IN del. In a further preferred embodiment, the attenuated virus comprises at least two mutations, one of which is in the ENV gene such as, e.g., ENV del, with one or more other mutations in any of the other genes of the virus. In a preferred embodiment, the one or more other mutations in the other genes of the virus are in genes selected from the group consisting of IN, CA, NC, Vif and ORF(2).

The invention also encompasses host cells infected with the attenuated virus and the progeny virus produced by such cells. Once produced, the attenuated virus may be purified from host cells using standard procedures.

Antibody production may be induced by infecting an animal with the attenuated virus or, alternatively, infected host cells may be used. If desired, the virus may be inactivated or the host cells fixed prior to administration to an animal and antibodies may be purified from animals using standard procedures.

In addition, the invention encompasses a vaccine that utilizes the attenuated whole virus discussed above or a host cell infected with one of these viruses. Again, the attenuated viruses may be inactivated and the host cells may be fixed. Such treatments may provide added assurance that vaccines will not themselves cause infection. Vaccines based upon one or more attenuated FIV-141 viruses or degenerate variants thereof may be used to induce protective immunity in a cat. Standard immunization protocols may be followed in administering vaccines so as to optimize the induction of protective immunity against subsequent challenge with FIV-141.

D. Compositions and Methods Based upon Mutated FIV-141 Genomic DNA

In another aspect, the present invention is directed to a substantially purified FIV-141 nucleic acid (DNA or RNA)

having a sequence corresponding to SEQ ID NO:1, or degenerate variant thereof, but which has been mutated to encode an attenuated virus. Mutations should be to one or more genes selected from the group consisting of Vif, MA, CA, NC, SU, TMf, ORF(2), CT, ENV, Vifn, Vifc, IN, DU, V3/4, V7/8, and RRE, and should be made in such a manner that, upon introduction into a host cell, a virus is made that has significantly reduced infectivity for feline T lymphocytes (or other susceptible cell types) relative to the wild type virus. Examples of several specific mutations that will produce an appropriate attenuated virus are described herein and include: MA del, ENV del, V3/4 del, V7/8 del, TMf del, CT del, Vif del, Vifc del, Vifn del, ORF(2) del, SU del, CA del, NC del, IN del, DU del, and RRE del. In a preferred embodiment, the attenuated virus comprises a combination of any two or more of the aforementioned mutations. In specific though non-limiting embodiments, the attenuated virus comprises double mutations in any of the following combinations of genes: (i) MA/TMf; (ii) MA/V3/4; (iii) MA/Vif; or (iv) ENV/IN. In a preferred embodiment, the attenuated virus comprises any of the following double deletions: (i) MA del/TMf del; (ii) MA del/V3/4 del; (iii) MA del/Vif del or (iv) ENV del/IN del. In a further preferred embodiment, the attenuated virus comprises at least two mutations, one of which is in the ENV gene such as, e.g., ENV del, with one or more other mutations in any of the other genes of the virus. In a preferred embodiment, the one or more other mutations in the other genes of the virus are in genes selected from the group consisting of IN, CA, NC, Vif and ORF(2).

The invention includes host cells transfected with the mutated nucleic acid and FIV progeny virus produced by the host cells.

Also included within the scope of the invention is a method of inducing the production of antibodies to FIV in an animal by injecting either nucleic acid mutated as described above or a host cell that has been transfected with the nucleic acid. If desired, the host cell may be fixed prior to administration. The antibodies produced may be purified using standard methods and used in assays designed to detect the presence of FIV.

The nucleic acid, preferably DNA, which has been mutated, may be used in a vaccine in which it is present at a concentration sufficient to induce protective immunity upon administration to a cat. Alternatively, a vaccine may include a host cell transfected with such DNA and, if desired, the host cell may be fixed after viral proteins are expressed. The vaccines may be administered to a cat at a dosage and for a duration sufficient to induce an immune response in a cat, and immunization protocols may be optimized for inducing protective immunity against subsequent infection by FIV-141.

E. Methods of Making and Using Attenuated Lentiviruses

The methods disclosed herein in connection with the production of attenuated FIV-141 may be effectively applied to the attenuation of other strains of FIV and to other types of lentivirus. A virus that has significantly reduced infectivity relative to its unmutated, wild type counterpart may be made by mutating one or more genes selected from the group consisting of MA, CA, NC, DU, ENV, SU, TMf, CT, Vif, ORF(2), Vifn, Vifc, IN, V3/4, V7/8, and RRE. In a preferred embodiment, the attenuated lentivirus comprises a mutation in the ENV gene. In a further preferred embodiment, the attenuated virus comprises a combination of any two or more of the aforementioned mutations. In specific though non-limiting embodiments, the attenuated virus comprises double mutations in any of the following combinations of genes. (i) MA/TMf; (ii) MA/V3/4; (iii) MA/Vif; or (iv) ENV/IN. In a preferred embodiment, the attenuated virus comprises any of the following double deletions: (i) MA del/TMf del; (ii) MA del/V3/4 del; (iii) MA del/Vif del or (iv) ENV del/IN del. In a further preferred embodiment, the attenuated virus comprises at least two mutations, one of which is in the ENV gene such as, e.g., ENV del, with one or more other mutations in any of the other genes of the virus. In a preferred embodiment, the one or more other mutations in the other genes of the virus are in genes selected from the group consisting of IN, CA, NC, Vif and ORF(2).

Mutations should be designed to eliminate or substantially reduce the activity of the gene product. This may be accomplished by deleting the entire gene or by deleting a large (e.g., one fourth) fraction of the entire gene. The invention encompasses the attenuated lentiviruses made using the disclosed methods, host cells infected with these viruses, and methods of inducing antibody production by injecting the attenuated virus into a mammal. The antibodies may be purified from infected mammals and used in immunoassays. Alternatively, the purified antibodies, or antibody-containing serum derived from animals infected with attenuated virus, may be used to treat a mammal for lentivirus infection.

As used herein, the phrase "induction of protective immunity", and the like, is used broadly to include the induction of any immune-based response in response to vaccination, including either an antibody or cell-mediated immune response, or both, that serves to protect the vaccinated mammal against the particular lentivirus. The terms "protective immunity", "protective response", "protect", and the like, as used herein, refer not only to the absolute prevention of any of the symptoms or conditions in the mammal resulting from infection with the particular lentivirus, but also to any detectable delay in the onset of any such symptoms or conditions, any detectable reduction in the degree or rate of infection by the particular lentivirus, or any detectable reduction in the severity of the disease or any symptom or condition resulting from infection by the particular lentivirus. Vaccine preparations according to the present invention should be administered at a dosage and for a duration sufficient to reduce one or more clinical signs and viral load associated with the infection of the mammal. When the lentivirus is a strain of FIV, the mammal treated will be a cat and the signs associated with the infection will include immunological abnormalities such as an abnormally low level of $CD4^+$ T-lymphocytes or an abnormally elevated number of $CD8^+$ T-lymphocytes. Other clinical signs will typically include alopecia, anemia, chronic rhinitis, conjunctivitis, diarrhea, emaciation, enteritis, gingivitis, hematochezia, neurological abnormalities and dermatitis.

The attenuated lentivirus (e.g., an attenuated strain of FIV), or host cells infected with such a virus, may be used in vaccine at a concentration sufficient to induce immunity when administered to a mammal (e.g., a cat). An immune response may then be induced by administering such a vaccine at a dosage and for a duration sufficient to induce protective immunity against subsequent infection by at least one strain of lentivirus.

F. Methods of Making and Using Mutated Lentivirus Nucleic Acid

The present invention is also directed to a method of producing a nucleic acid suitable for use in a vaccine against lentivirus, e.g. FIV, infection. This is accomplished by reverse transcribing the genomic RNA of the lentivirus; cloning the reverse transcript; mutating one or more genes selected from the group consisting of MA, CA, NC, SU, TMf, ORF(2), CT, ENV, Vif, Vifn, Vifc, V3/4, V7/8, IN, DU, and RRE; and then cloning the mutated nucleic acid. Preferably, mutations should be such that, upon introduction into a host cell, an attenuated virus is made that has significantly reduced infectivity relative to lentivirus produced by the unmutated, wild type nucleic acid. In the case of FIV, infectivity should be reduced or eliminated for feline T-lymphocytes.

Mutated lentivirus nucleic acid may be purified and used to transfect host cells, make progeny virus, and make antibody in the same way as described above for FIV-141. In addition, the nucleic acid, or host cells transfected with the nucleic acid, may be incorporated into a vaccine and used to induce protective immunity in a mammal. Preferably, the nucleic acid will encode an attenuated strain of FIV that has significantly reduced infectivity in feline PBMCs, including T-lymphocytes such as FeP2 cells. Under these circumstances, the immune response will be induced in a cat.

BRIEF DESCRIPTION OF THE DRAWINGS

FIG. 11: Cumulative viral RNA loads detected by QcRT-PCR in plasma samples obtained from cats vaccinated with plasmids encoding particular deletion mutants of FIV-141 and then challenged with FIV-141. Cats in the positive placebo group were vaccinated with pCR-Script SK(+) vector DNA and then challenged with FIV-141. Cats in the negative placebo group were vaccinated with pCR-Script SK(+) vector DNA, but were not challenged with FIV-141.

DETAILED DESCRIPTION OF THE INVENTION

Figure 1:
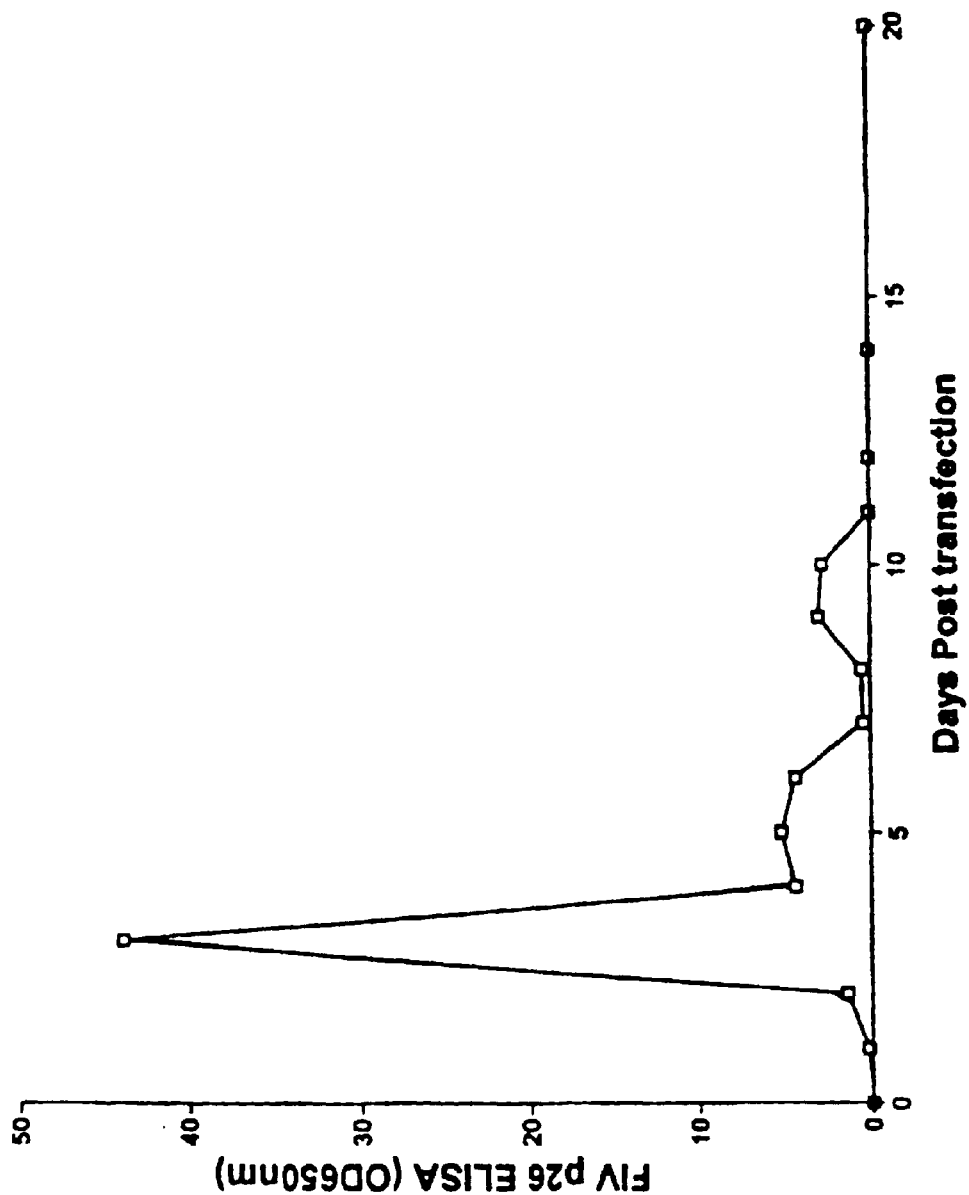
FIG. 1: FIV Production from Transfected Cells. Crandell Feline Kidney (CRFK) cells were transfected with a plasmid comprising the full length FIV-141 genome. Beginning at 24 hours post-transfection, cell supernatants were harvested and assayed for the presence of FIV p26 capsid protein using an enzyme immunoassay.

A. Production of FIV-141 and DNA Encoding the Virus

The present invention is directed to a novel strain of feline immunodeficiency virus (designated herein "FIV-141") that is distinguished from all similar strains based upon its genomic nucleic acid sequence and biological functions. Although the genome of FIV-141 consists of RNA, this is reverse transcribed into DNA and integrated into the genome of an infected host. It will be understood that references made herein to sequences of FIV and to mutated forms of such sequences encompass both the reverse transcribed viral RNA sequences as well as the corresponding DNA itself.

It is well known that techniques such as site-directed mutagenesis may be used to introduce variations into the structure of nucleic acids. Mutations in the FIV-141 nucleic acid sequence introduced by this or some similar method are encompassed by the invention, provided that at least one major biological characteristic of the resulting virus, e.g., its antigenicity, remains substantially the same as that of the virus from which it was derived. In a preferred though non-limiting embodiment, mutations that detectably reduce the infectivity of FIV-141 compared to that of the wild-type strain fall within the scope of the invention. For example, a specific mutation in the ENV gene is described herein below which produces a virus that replicates, but which shows greatly reduced infectivity. The present invention includes both this mutation and other mutations that result in substantially reduced viral infectivity.

As discussed in the Examples section, the complete FIV-141 genome has been cloned and a plasmid containing the full length sequence has been deposited as ATCC number 203001. Standard methodology may be used to isolate this plasmid and transfect it into host cells capable of supporting virus production. Crandell feline kidney (CRFK) cells have been found to be suitable for this purpose, but other cell types such as, e.g., feline T lymphocyte cells, may be used as well. In some cases, host cells expressing the virus may be used directly, e.g., they may be harvested and used to generate antibodies or in a vaccine. Alternatively, the virus produced in the cells may be isolated in highly purified form using known separation techniques such as sucrose-gradient centrifugation. Such methods are effective both for the wild type virus and for mutant forms of the virus.

An alternative method for obtaining the FIV-141 genome is to perform PCR amplification using primers corresponding to sequence elements in SEQ. ID NO:1. In general, the primers should be about 20 to 50 bases in length. A strategy may be designed for amplifying the entire FIV-141 genome or, alternatively, portions of the genome may be amplified separately and then joined together to form the full length sequence. The Examples section below describes specific primers and methods that have been found to be effective, but alternative procedures may be developed and used as well.

If virus is being isolated from a natural source, then primers for PCR should correspond to sequences unique to FIV-141. Successful amplification using such primers will indicate that a virus responsible for an infection is, in fact, FIV-141. Thus, PCR may be used both diagnostically, as well as in methods for isolating virus.

B. Production of Inactivated Virus and Fixed Host Cells The FIV-141 virus, or a degenerate variant thereof, may be used to generate antibodies in an appropriate host and in vaccines. In either case, it will usually be desirable to inactivate the virus prior to administering it to an animal. Inactivation may be accomplished by any means known in the art. For example, virus may be purified and then inactivated by incubation for about 24 hours in 0.8% formalin or 1.25% paraformaldehyde. Such procedures may be used either with wild type or mutant viruses.

Antibodies may also be generated or immunizations accomplished using host cells infected with FIV-141, mutated forms of the virus, or degenerate variants thereof. Any host cell capable of supporting viral replication may be used including peripheral blood mononuclear cells (PBMCs). Ordinarily, cells should be fixed prior to administration to an animal. Fixing may be performed by treating cells with paraformaldehyde (e.g., 1.25%) for a period of about 24 hours at 37° C. The other methods discussed above for inactivating virus may also be used for fixing cells, as may any other method disclosed in the art.

C. Production of Attenuated Virus

As discussed above, vaccines may be produced using either inactivated virus or fixed host cells. An alternative method is to use a virus that has been attenuated by mutating one or more genes in the viral genome. The objective is to produce a virus that is not infectious when administered to a cat. Rates of viral replication can be determined in vitro by infecting cells (e.g., PBMCs) with virus, and then determining how the levels of virus change with time. Replication can be followed using an immunological assay that measures an antigen specific for FIV, by quantitative PCR, or by measuring the activity of an enzyme specific to the virus (e.g., reverse transcriptase). Infectivity can be determined by exposing feline T lymphocytes (e.g., FeP2 cells) to virus and determining the extent to which the cells take up the virus and support replication (see Example 4 below).

Mutations in the FIV-141 genome may be made by site-directed mutagenesis. One way to carry this out is to amplify viral genes with primers that introduce alterations into the normal gene sequence. For example, unique restriction sites may be introduced in a selected region of the genome and the sequence between such sites may then be excised by restriction enzyme digestion. After excision, the remaining portion of genomic DNA may be religated and then introduced into an appropriate host cell to produce mutated virus. A detailed description of the making and testing of mutated viruses and mutated viral genomes is provided in Examples 3 and 4 below. A summary of various mutations that have been introduced may be found in Table 1.

TABLE 1

Mutations in FIV-141

| MUTATION | NUCLEOTIDES DELETED | AMINO ACIDS DELETED |
|---|---|---|
| MA del | 123 bases, nucleotides 879–1001 | 41 amino acids, residues 85–125 at the C-terminus of the MA protein |
| CA del | 114 bases, nucleotides 1056–1169 | 38 amino acids, residues 9–46 at the N-terminus of the CA protein |
| NC del | 242 bases, nucleotides 1635–1876 | 21 amino acids in the CA region and 51 amino acids in the NC region, accompanied by a reading frame shift preventing expression of the terminal portion of the NC protein |
| ENV del | 2103 bases deleted, nucleotides 6577–8679 | 701 amino acids from the middle of the ENV protein, residues 106–806 |
| SU del | 1509 bases, nucleotides 6577–8085 | 503 amino acids of the SU protein, residues 106–608 |
| V3/4 del | 432 bases, nucleotides 7339–7770 | 144 amino acids of the V3 and V4 regions of SU, residues 360–503 |
| V7/8 del | 216 bases, nucleotides 8380–8595 | 72 amino acids from the V7 and V8 variable regions of the TM protein, residues 98–169 |
| TMf del | 75 bases, nucleotides 8071–8145 | 25 amino acids in the cleavage junction between SU and TM |
| CT del | 138 bases, nucleotides 8686–8823 | 46 amino acids from the cytoplasmic domain of TM |
| DU del | 345 bases, nucleotides 4019–4363 | 115 amino acids from the DU protein, residues 9–123 |
| IN del | 669 bases, nucleotides 4418–5086 | 223 amino acids of the IN protein, residues 9–231 |
| Vifn del | 150 bases, nucleotides 5286–5435 | 50 amino acids from the N-terminal portion of the Vif protein, residues 19–68 |
| Vifc del | 438 bases, nucleotides 5436–5873 | 146 amino acids from the C-terminal portion of Vif, residues 69–214 |
| Vif del | 588 bases, nucleotides 5286–5873 | 196 amino acids from the Vif protein, residues 19–214 |
| Orf(2) del | 237 bases, nucleotides 5988–6224 | 79 amino acids of the ORF(2) protein |
| RRE del | 84 bases, nucleotides 8827–8910 | — |

Examples of several specific mutations that produce attenuated viruses suitable for administration to animals to induce antibody production or for use in vaccines are MA del, ENV del, V3/4 del, V7/8 del, TMf del, CT del, Vif del, Vifc del, Vifn del, ORF(2) del, CA del, NC del, SU del, IN del, DU del, and RRE del. Thus, viruses mutated in any of the Vif, MA, ORF(2), ENV, Vifn, Vifc, V3/4, V7/8, TMf, CT, SU, CA, NC, IN, DU, or RRE genes are attenuated, and other nucleotide deletions or alterations that inactivate these genes should produce viruses with similar characteristics.

D. Generation of Antibodies to FIV-141 and Treatment of Infected Cats

Antibodies to FIV-141 can be produced in any of the animals typically used for antibody production, including mice, rabbits, etc. However, it is preferred that the antibodies be produced in cats. If wild type virus is used as antigen, the virus should be inactivated prior to administration. When attenuated viruses are used, e.g., viruses mutated so as to reduce or eliminate their infectivity, inactivation or the fixing of host cells is not required, although these procedures may be performed if desired.

Compositions containing virus may be administered to animals by any route, but animals will typically be injected intramuscularly, subcutaneously or intravenously. Generally, the virus preparation will include an adjuvant, e.g., Freund's complete or incomplete adjuvant. Appropriate preparations for injection, injection schedules and the like are well known in the art and may be employed for FIV-141 and its mutants (see, e.g, Harlow, et al., 1988, *Antibodies, A Laboratory Manual*, Cold Spring Harbor Laboratory, N.Y.; Klein, 1982, *Immunology: The Science of Self-Nonself Discrimination*). Monoclonal antibodies may also be used, and can be made using standard procedures (Kennett, et al, 1980, *Monoclonal Antibodies and Hybridomas: A New Dimension in Biological Analyses*; Campbell, 1984, "Monoclonal Antibody Technology," in: *Laboratory Techniques in Biochemistry and Molecular Biology*).

Antibodies or fragments of antibodies reacting with specificity to FIV-141 (i.e., having at least a 100 fold greater affinity for FIV-141 than for any other virus) may also be used in any of a variety of immunoassays. For example, the antibodies may be used to detect FIV-141 in radioimmunoassays or in immunometric assays, also known as "2-site" or "sandwich" assays (see Chard, 1978, "An Introduction to Radioimmune Assay and Related Techniques," in: *Laboratory Techniques in Biochemistry and Molecular Biology*, North Holland Publishing Co. N.Y.). In a typical immunometric assay, a quantity of unlabeled antibody is bound to a solid support that is insoluble in the fluid being tested, e.g., blood, lymph, cellular extracts, etc. After the initial binding of antigen to immobilized antibody, a quantity of detectably labeled second antibody (which may or may not be the same as the first) is added to permit detection and/or quantitation of antigen (see, e.g., Kirkham et al. (ed.), 1970, *Radioimmune Assay Methods*, pp. 199–206, E&S Livingstone, Edinburgh). Many variations of these types of assays are known in the art and may be employed for the detection of FIV.

E. Conventional Vaccines and Vaccination Procedures

Vaccines and vaccination procedures employing different strains of FIV or closely related viruses have been discussed by a number of authors (Elyar et al., 1997, Vaccine 15:1437–1444; Yamamoto et al., 1993, J. Virol. 67:601–605; Murphey-Corb et al., 1989, Science 240:1293–1297; Jarrett et al., 1990, AIDS 4:S163–S165; and Desrosiers et al., 1989, Proc. Nat'l Acad. Sci. USA 86:6353–6357). In the case of FIV-141, there are three types of vaccines that may be used: inactivated whole virus vaccine, fixed cell vaccines, and attenuated virus vaccines.

Typically, a vaccine will contain between about $1\times10^6$ and about $1\times10^8$ virus particles in a volume of between about 0.5 and 5 ml. Formulation may take place using standard methods such as those described in *Remington's Pharmaceutical Sciences*, 1982, Mack Publishing Co., Easton, Pa. 16th ed. Preparations may contain inactivated virus, fixed host cells or attenuated virus, together with a pharmaceutically or veterinarily acceptable carrier as known in the art and one or more adjuvants. Vaccines will generally be designed for parenteral administration, although the present invention is compatible with other forms of administration as well, such as e.g., by oral, intranasal, intramuscular, intra-lymph node, intradermal, intraperitoneal, subcutaneous, rectal or vaginal administration, or by a combination of routes. The skilled artisan will readily be able to formulate the vaccine composition according to the route chosen.

The most preferred vaccines will contain attenuated virus that is completely, or essentially completely, non-infectious when administered to cats.

Immunization procedures will typically involve several inoculations with vaccine (e.g., 3 inoculations) separated by intervals of 3 to 10 weeks. Procedures for optimizing inoculation schedules and the other parameters associated with immunization are well known in the art.

F. DNA Vaccines

References describing vaccines and vaccination procedures that utilize nucleic acids (DNA or mRNA) include U.S. Pat. No. 5,703,055, U.S. Pat. No. 5,580,859, U.S. Pat. No. 5,589,466, International Patent Publication WO 98/35562, and various scientific publications, including Ramsay et al., 1997, Immunol. Cell Biol. 75:360–363; Davis, 1997, Cur. Opinion Biotech. 8:635–640; Manickan et al., 1997, Critical Rev. Immunol. 17:139–154; Robinson, 1997, Vaccine 15(8):785–787; Robinson et al, 1996, AIDS Res. Hum. Retr. 12(5):455–457; Lai and Bennett, 1998, Critical Rev. Immunol. 18:449–484; and Vogel and Sarver, 1995, Clin. Microbiol. Rev. 8(3):406–410, which are incorporated herein by reference. These procedures may be utilized to produce a vaccine against FIV in which nucleic acid corresponding to attenuated FIV-141, or a degenerate variant thereof, is administered to a cat. Immunogens delivered in this manner typically evoke both a humoral and cytotoxic immune response.

Either DNA or RNA encoding the attenuated FIV-141 genome, or degenerate variant thereof, may be used in vaccines, but DNA will generally be preferred. The DNA may be present in a "naked" form or it may be administered together with an agent facilitating cellular uptake (e.g., liposomes, or cationic lipids). The polynucleotide molecule may be associated with lipids to form, e.g., DNA-lipid complexes, such as liposomes or cochleates. See, e.g., International Patent Publications WO 93/24640 and WO 98/58630, which are incorporated herein by reference.

The typical route of administration will be by intramuscular injection of between about 0.1 and 5 ml of vaccine. The total polynucleotide in the vaccine should generally be between about 0.1 ug/ml and about 5.0 mg/ml. Polynucleotides may be present as part of a suspension, solution or emulsion, but aqueous carriers are generally preferred.

Immunization of cats using DNA vaccines may be performed as either a single inoculation or as multiple inoculations of divided doses separated, e.g., by intervals of 3 to 10 weeks. If desired, serum may be collected from inoculated animals and tested for the presence of antibodies to FIV-141 or other strains of FIV.

G. Extension of Methodology to other Lentiviruses

The methods discussed above for attenuating FIV-141 and for producing mutated viral nucleic acids suitable for use in vaccines may be extended to other strains of FIV and to other types of lentivirus. In each case, the viral genome is cloned and mutated in one or more genes selected from the group consisting of: MA, CA, NC, DU, ENV, SU, TMf, CT, ORF(2), Vif, Vifn, Vifc, V3/4, V7/8, IN, and RRE. The mutation should be designed to inactivate the gene product. This can usually be most easily accomplished by deleting either the entire gene or a substantial portion of the gene. Although the specific methodology used for inducing mutations will vary depending upon the virus, the basic techniques are routine in the art and, using the procedures disclosed herein as a guide, can be readily carried out by a skilled molecular biologist. Antibody production, the making and administration of vaccines, etc., may be accomplished as discussed in connection with FIV-141 herein, making minor adaptations as needed.

In addition, it is contemplated that antibodies to certain lentiviruses may be used to provide passive immunity to an animal or human infected with the virus. Either purified antibody or antibody-containing serum may be used for this purpose, and preparations may be administered on a periodic

EXAMPLES

Example 1:
Construction of an Infectious FIV Proviral DNA Clone
A. Isolation and Cloning of FIV-141
Virus Isolation FIV-141 was isolated from the plasma of an FIV-infected cat. The virus was amplified by administering plasma from the infected animal to a specific pathogen-free (SPF) cat. Infection of the inoculated cat was confirmed by virus isolation and seroconversion. The cat was euthanized 12 weeks post challenge, tissues were collected, and the spleen was used as the source of virus for the molecular cloning of the FIV-141 genome. Genomic DNA was isolated from the infected spleen using a DNA extraction kit (Stratagene, La Jolla, Calif.) according to the protocol provided by the manufacturer. Purified genomic DNA was dissolved in TE buffer at a concentration of 1 ug/ml and stored a −70° C.

PCR Amplification and Cloning of Three Segments of the FIV-141 Genome

Three sets of oligonucleotides were designed based upon the published sequences of other FIV isolates (Talbott et al., 1989, Proc. Nat'l Acad. Sci. USA, 86:5743–5747; Miyazawa et al., 1991, J. Virol. 65:1572–1577; Talbott et al., 1990, J. Virol. 64:4605–4613). These oligonucleotides were used to amplify three segments of the FIV-141 genome, one at the 5' end, one at the 3' end and one in the middle of the genome. Because of a low copy number of the FIV proviral genome in infected tissue, two rounds of PCR amplification were performed using a semi-nested set of primers for each segment.

Three primers were used to clone a segment from the 5' end of the FIV-141 proviral genome, extending from nucleotides 118 to 646. This region covers most of the 5' long terminal repeat, the intervening sequence between the 5' long terminal repeat and the Gag open reading frame, and the N-terminal portion of the Gag gene. The sequences of the primers were as follows: the forward primer pr-1 (117-CCGCAAAACCACAT CCTATGTAAAGCTTGC-146, SEQ ID NO:2) and the two reverse primers, pr-2 (646-CGCCCCTGTCCATTCCCCATGTTGCTGTAG-617, SEQ ID NO:3) and pr-8 (1047-TTACTGTTTGAATAG-GATATGCCTGTGGAG-1018, SEQ ID NO:4). First round PCR amplification was performed using 200 ng each of pr-1 and pr-8 as primers and 1 ug of genomic DNA as template, with a mixture of 0.5 units of Taq DNA polymerase (Gibco, BRL Gaithersburg, Md.) and 1 unit of Pfu DNA polymerase (Stratagene, La Jolla, Calif.). Amplification proceeded at 94° C. for one minute; followed by 30 cycles of denaturing at 94° C., for 45 seconds; annealing at 52° C. for 45 seconds; and extension at 72° C. for two minutes. The second round amplification was performed using primers pr-1 and pr-2 together with 2 ul of the first round PCR products as template. The same conditions used in the first round of amplification were applied in the second round, except that annealing took place at a temperature of 55° C.

Three oligonucleotides were also used to clone a segment from the 3' end of the FIV-141 proviral genome. This segment includes nucleotides 8874 to 9367, consisting of most of the 3' long terminal repeat and the intervening sequence between the 3' long terminal repeat and the ENV gene. The sequences of the three primers were as follows: the two forward primers, pr-5 (8793-GCAATGTGGCATGTCTGAAAAAGAGGAGGA-8822, SEQ ID NO:5) and pr-7 (8874-TCTTCCCTTTG-AGGAAGATATGTCATATGAATCC-8907, SEQ ID NO:6), and the reverse primer, pr-6 (9367-TCTGTGGGAGCCTCAAGGGAGAACTC-9342, SEQ ID NO:7). Primers pr-5 and pr-6 were used to perform the first round amplification, and pr-6 and pr-7 were used to carry out the second round of amplification. The same conditions were applied to the present amplification as those used in the amplification of the segment from the 5' and of FIV-141 described above.

In order to clone a segment from the middle part of the FIV-141 genome, extending from nucleotides 5147 to 5631 and covering the C-terminal portion of the IN gene and the N-terminal portion of the Vif gene, a first round amplification was performed using the forward primer, pr-3 (4738-ACAAACAGATAATGGACCAAATTTTAAAAAA-4767, SEQ ID NO:8) and the reverse primer pr-10 (5631-TTTCAATATCATCCCACATAAATCCTGT-5604, SEQ ID NO:9). A second round amplification was performed using forward primer pr-9 (5147-TTAAAGGATGAAGAG-AAGGGATATTTTCTT-5176, SEQ ID NO:10) and reverse primer-pr-10.

After the completion of the second round of PCR amplification, the products were applied to a 1% agarose gel and the expected bands for all three regions were purified by a Wizard PCR Preps kit (Promega, Madison, Wis.). The purified PCR fragments were cloned into pCR-Script Amp SK(+) vectors (Stratagene, La Jolla, Calif.) according to the procedure recommended by the manufacturer. Inserts were confirmed by restriction enzyme digestion followed by sequencing the two strands of the plasmid DNA (Advanced Genetic Analysis Center, St. Paul, Minn.). In order to eliminate "errors" in the FIV sequences generated by the DNA polymerases during amplification, three clones from three independent PCR amplifications were sequenced for each region. The consensus sequence from the three independent clones was considered as the authentic FIV-141 sequence.

Combining the sequences from the 5' and 3' end segments suggests that the long terminal repeat of FIV-141 consists of 354 bases, including 208 bases in the U3 region, 79 bases in the R region and 67 bases in the U5 region. The terminal 2-base inverted repeats, the TATA box, the polyadenylation signal, and a number of putative cis-acting enhancer-promoter elements were perfectly conserved relative to other FIV isolates.

PCR Amplification and Cloning of the Entire Proviral Genome of FIV-141

Sequence information obtained using the three cloned segments described above was used to design FIV-141 specific primers that could be used to amplify and clone the entire proviral genome in two pieces, the 5' half and the 3' half. Each half was amplified by two rounds of amplification with a semi-nested set of primers.

To amplify the 5' half of the FIV-141 genome (from nucleotide 1 to 5460), the first round of amplification was performed using forward primer, pr-11 (1-TGGGAAGATTATTGGGATCCTGAAGAAATA-30, SEQ ID NO:11) and the reverse primer pr-10. The amplification protocol followed that provided with the Advantage Genomic PCR Kit from Clonetech (Palo Alto, Calif.). Briefly, the PCR reaction was set up in a total volume of 50 ul, containing 1 ul of genomic DNA template (1 ug/ul), 1 ul of each primer (100 ng/ul), 5 ul of the 10×Tth PCR reaction buffer, 2.2 ul of 25 mM Mg (OAc)$_2$, 1 ul of 50×dNTP mix (10 mM each), 1 ul of 50×Advantage Tth Polymerase mix, 1 ul of Pfu polymerase (2.5 U/ul), and 36.8 ul of sterile water. The reaction mix was heated at 94° C. for 2 minutes, followed by 30 cycles of amplification: 94° C. for 30 seconds and 68° C. for 6 minutes. The second round amplification was carried out using 2 ul of the first round PCR product as template, the same forward primer pr-11 and the reverse primer, pr-12 (5460-CATAT- CCTATATAATAATCACGCGTATGAAAGCTCC-ACCT- 5421, SEQ ID NO:12). To facilitate the construction of a full length FIV-141 genome from the two halves, the restriction enzyme site Mlu I (underlined) was incorporated into the primer pr-12. The same PCR conditions as used in the first round amplification were applied in the second round and resulted in the production of an amplification fragment with the size of 5460 base pairs.

To clone the 3' half of the FIV-141 proviral genome, three primers, pr-9, pr-13 and pr-14, were initially used to perform amplifications. The first round PCR amplification was carried out using forward primer, pr-9 and reverse primer, pr-14 (9464-TGCGAGGTCCCTGGCCCGGACTCC-9441, SEQ ID NO:13). The second round amplification was performed using forward primer, pr-13 (5421-AGGTGGAGCTTTCA TACGCGTGATTATTATATAGGATATG-5460, SEQ ID NO: 14) and the same reverse primer pr-14. Primer pr-13 was designed to overlap with pr-12 primer used in the amplification of the 5' half of the genome. As in the pr-12 primer, an Mlu I restriction enzyme site (underlined) was incorporated into pr-13 to facilitate the construction of the full-length FIV clone. Unfortunately, after two rounds of PCR amplification, no specific DNA band was observed. It was concluded that the failure to amplify the 3' half of the FIV-141 genome was probably due to the high GC content and very stable secondary structure in primer pr-14. Therefore, a new primer, pr-16 (9444-CTCCAGGGATTCGCAGGTAAGAGAAATTA-9416, SEQ ID NO:15) was designed. This sequence ends 20 bases upstream of the last base in the FIV-141 genome. First round PCR amplification was performed using forward primer pr-9 and reverse primer pr-16. This was followed by amplification using forward primer pr-13 and, again, reverse primer pr-16. A DNA fragment with the expected size was obtained after the second round amplification.

The DNA fragments of the 5' half and 3' half of the FIV-141 genome were purified using the Wizard PCR Preps DNA purification kit (Promega, Madison, Wis.), and cloned into pCR-Script Amp SK(+) cloning vectors (Stratagene, La Jolla, Calif.). Three clones from three independent PCR reactions were sequenced for each of the 5' half and 3' half clones. Both strands of plasmid DNA were sequenced and the authentic consensus sequence for the entire genome was obtained by comparing the results obtained for the three independent clones. The DNAStar program (DNAStar Inc., Madison, Wis.) was used to perform sequence assembly, comparison and analysis.

B. Molecular Characterization of the Cloned FIV-141 Virus

Sequence Results and Analysis of the Entire FIV-141 Genome

The entire proviral genome of FIV-141 was found to contain 9464 bases. The genome is organized in a manner typical of lentiviruses and consists of: 5' and 3' long terminal repeats; three large open reading frames (ORF) containing the Gag, Pol, and ENV genes; and three small open reading frames containing the Vif, Rev, and ORF(2) regulatory proteins. The long terminal repeat shares 78.6% and 93.9% sequence homology with FIV-Petaluma (Olmsted et al., 1989, Proc. Nat'l Acad. Sci. USA 86:2448–2452) and FIV-USIL (Sodora et al., 1995, AIDS Res. Hum. Retroviruses 11:531–533) isolates, respectively. The Gag polyprotein shares 88.4% and 94.4% amino acid homology with FIV-Petaluma and FIV-USIL isolates, respectively.

The Gag gene encodes the matrix (MA) protein (bases 627 to 1031), capsid (CA) protein (bases 1032 to 1724), and nucleocapsid (NC) protein (bases 1725 to 1976). The Gag and Pol polyprotein overlap 97 bases with the Pol ORF, beginning at nucleotide 1880 and ending at nucleotide 5239. A heptanucleotide frameshift signal (5'-GGGAAAC-3') is located 100 bases upstream of the 3' end of the overlap. As the result of a −1 frameshift during translation, a Gag/Pol polyprotein fusion is produced.

Compared with FIV-Petaluma and FIV-USIL isolates, the Pol polyprotein of FIV-141 exhibits an 85.7% and 92.2% amino acid identity, respectively. The Pol gene encodes: a lead sequence from nucleotide 1880 to 1978; a protease (PR) from nucleotide 1979 to 2326; a reverse transcriptase (RT) from nucleotide 2327 to 3994; a deoxyuridine triphosphatase (DU) from nucleotide 3995 to 4393; and an integrase (IN) from nucleotide 4394 to 5239.

The Vif ORF overlaps eight bases with the Pol gene, and shares 80.2% and 91.3% amino acid homology with FIV-Petaluma and FIV-USIL isolates, respectively. Immediately following the Vif gene is the ORF(2) gene, beginning at nucleotide 5988 and ending at 6224, which evidences a 62% and 92.4% sequence homology with FIV-Petaluma and FIV-USIL isolates, respectively.

The ENV polyprotein shares a 79.3% and 88.6% amino acid identity with FIV-Petaluma and FIV-USIL isolates, respectively. The ENV gene encodes: a surface (SU) protein, from nucleotide 6262 to 8088; and a transmembrane (TM) protein, from nucleotide 8089 to 8826.

The Rev protein results from the translation of a multiple splicing mRNA. The first exon of the putative Rev gene apparently shares an initiation codon with the ENV gene, beginning at nucleotide 6262 and ending at 6505. The second Rev exon begins at nucleotide 8947, extends into the U3 region of the 3' long terminal repeat, and ends at nucleotide 9161. The Rev protein of FIV-141 has a 67.3% and 83.9% amino acid homology with FIV-Petaluma and FIV-USIL isolates, respectively. The 151 base Rev responsible element (RRE) overlaps 52 bases with the ENV gene, beginning at nucleotide 8775 and ending at 8925.

Based on the sequence comparisons within the V3 region of the SU glycoprotein, FIV-141 is a type B isolate. Apparently, FIV-141 is most closely related to FIV-USIL, another type B FIV isolate.

C. Construction of a Full-Length Molecular Clone of FIV-141

In order to construct a full-length FIV-141 clone, the 20 bases at the extreme 3' end of the genome had to be added to the 3' half clone. In addition, a consensus sequence was identified by comparing the sequences from three independent clones. Site directed mutagenesis (SDM) was then used to adjust the sequences of the 5' and 3' half clones to match that of the consensus before construction of the full length viral clone.

Addition of Missing 20 Bases at the Extreme 3' End of FIV-141

In order to add the 20 bases to the 3' half clone of FIV-141, the long terminal repeat was first PCR amplified and cloned into a pCR-Script Amp SK(+) cloning vector using the 5' half clone as template and forward primer, PR-21 (5'-TTACAAGAATTCAACTGCAGTGGGAA GATTATT-GGGATCCTGAAGAAAT-3', SEQ ID NO:16) and reverse primer, pr-20 (5'-TTCAAGGAGCTCTTTTGTCGACA-ACTGCGAGGTCCCTGGCCC-3', SEQ ID NO:17). In order to facilitate cloning the PCR fragment, two restriction enzyme sites (underlined), EcoRI and Pst I, were incorporated into the forward primer, PR-21, and two sites (underlined), Sac I and Sal I, were incorporated into the reverse primer, PR-20. The FIV-141 specific sequences in the primers are shown in italics. The resulting clone was sequenced and designated as pCR-LTR. A restriction fragment of pFIV-LTR generated by digestion with Sac I and Nhe I was cloned into one of the 3' half clones of FIV-141. The resulting clone was named pFIV3'-2A-1+ and the presence of the 20 bases at the extreme 3' end of FIV-141 was confirmed by nucleotide sequencing.

Construction of Consensus Sequence in the 5' and 3' Half Clones

In order to establish the consensus sequence in the existing 5' and 3' half clones of the FIV-141 genome, SDM was performed. To introduce sequence changes in the first half of the genome, one of the 5' half clones (designated as "pFIV5'-D-11") was used as template. There were a total of 15 nucleotide changes in pFIV5'-D-11 compared to the consensus sequence. Two changes were located in the 5' non-coding region, A602G and A612G, and seven nucleotide changes in the coding region were silent mutations. The other six changes in the coding region resulted in an amino acid substitution for each change, three in the RT region (an A2890G nucleotide change, resulting in an I to M amino acid substitution; a G3461A change resulting in an E to K substitution; and a G3737A change resulting in an E to K substitution), one in the DU protein (a C4383T change, resulting in a T to I substitution), and two in the IN protein (an A4579G change, resulting in an I to M substitution; and an A5007T change, resulting in a Q to L substitution). Seven oligonucleotides were designed to make the two changes in the non-coding region and six changes in the coding region leading to amino acid substitutions. The oligonucleotides are as follows, with mismatches underlined:

Oligo pF-1, designed to repair the A602G and A612G errors: 5'-GATTCGTCG GGGGACAGCCAAC AAGGTAGGAGAGATTCTACAGCAACATGGGG-3' (SEQ ID NO:18);

Oligo pF-2, designed to fix the error A2890G: 5'-TCAATATATGGATGATA TCTATATAGGAT-CAAATTTAAGTAA-3' (SEQ ID NO:19);

Oligo pF-3, designed to repair the error G3461A: 5'-GTGATATAGCTCTAAG GGCATGTTA-CAAAATAAGAGAAGAATCCATTATAAGAA-TAGG-3' (SEQ ID NO:20);

Oligo pF-4 was designed to repair the error G3737A: 5'-CGGGCAGATG GCAGGTAATGGAAATA-GAAGGAAGTAATCAAAAAGC-3' (SEQ ID NO:21);

Oligo pF-5, designed to repair the error C4383T: 5'-AGAAAGGGATTTGG GTCAACTGGAGTCTTT-TCTTCATGGGTGGA-3' (SEQ ID NO:22);

Oligo pF-6, designed to repair the error A4579G: 5'-GGGGGACAATTAAA GATTGGACCTGGCAT ATGGCAAATGGACTGTACACAC-3' (SEQ ID NO:23); and Oligo pF-7, designed to repair the error A5007T: 5'-GGCTCCTTATGAATTA TACATACAAC AGGAATCATTAAGAATACAAGAC-3' (SEQ ID NO:24).

In order to make sequence changes in the 3' half of the genome, the 3' half clone "pFIV3'-2A-1+" was used as a template in performing SDM. There were nine changes in the pFIV3'-2A-1+ clone compared to the consensus sequence. Two nucleotide changes in the coding region were silent. The other seven changes all resulted in an amino acid substitution: one in the Vif protein (T5508C, H to Y); one in the ORF(2) region (A6041T, D to E); three in the SU protein (A6922G, V to I; G7007T, T to R; and A7814G, S to N); one in the TM region (A8405T, I to N); and one in the Rev region (A8976G, E to K). Seven mutagenesis oligonucleotides were designed for repairing these seven amino acid substitutions:

Oligo pF-8, designed to repair the error T5508C: 5'-CAAAATAGTTTAAGATTGTATGTTTATAT-AAGCAAT-3' (SEQ ID NO:25);

Oligo pF-9, designed to repair the error A6041T: 5'-CAGAAAAGTTAGATAGA GAAGCAGCT-ATTAGATTGTTTAT-3' (SEQ ID NO:26);

Oligo pF-10, designed to repair the error A6922G: 5'-TAAAAGCAAATGTTA ATATAAGTATACAA-GAAGGACCTAC-3' (SEQ ID NO:27);

Oligo pF-11, designed to repair the error G7007T: 5'-AAAAGCTACAAGGCAATGCAGAAGG GGAAGGAT- ATGGAAG-3' (SEQ ID NO:28);

Oligo pF-12, designed to repair the error A7814G: 5'-AGAGGACCTTATTGT ACAATTTAATATGA-CAAAAGCAGTGGAAA-3' (SEQ ID NO:29);

Oligo pF-13, designed to repair the error A8405T: 5'-CCCTCAATCTGTGG ACAATGTATA ACATGACTATAAATCA-3' (SEQ ID NO:30);

Oligo pF-14, designed to repair the error A8976G: 5'-GACAACGCAGAAGAA GAAAGAAGAAGGC-CTTCAAAAAATT-3' (SEQ ID NO:31).

Single stranded DNA template preparations for both clones, pFIV5'-D-11 and pFIV3'-2A-1+, were made essentially by the protocol provided by the manufacturer (Promega, Madison, Wis.). Briefly, DNA plasmids of the two clones were transfected into the E. coli strain CJ236. Single stranded (SS) DNA was rescued using helper phage R408 and purified by phenol/chloroform extraction. Purified SS DNA was dissolved in TE buffer with its concentration being estimated by running 2 ul samples of template preparations on a 1% agarose gel. Oligonucleotides were phosphorylated according to the protocol provided by the manufacturer (Gibco BRL, Gaithersburg, Md.).

Oligonucleotides were annealed to template in a total reaction volume of 30 ul. This contained 0.2 pmol of single-stranded DNA template (pFIV5'-D-11 or pFIV3'-2-A-1+), 4 pmol of each oligonucleotide (i.e., pF-1 to pF-7 for the pFIV5'-D-11 template and pF-8 to pF-14 for the pFIV3'-2-A-1+ template), 3 ul of annealing buffer (0.2 M Tris-HCl, pH 7.4, 20 mM MgCl$_2$, and 0.5 M NaCl). The mixture was incubated at 85° C. for 5 minutes and then gradually cooled to room temperature at a rate of approximately 1° C. per minute.

In order to synthesize the complementary DNA strand, the following components were added to the annealing mixture: 3 ul of synthesis buffer (4 mM of each dNTP, 7.5 mM ATP, 175 mM Tris-HCl, pH 7.4, 37.5 mM MgCl$_2$, 215 mM DTT), 3 ul of T4 DNA ligase (3 U/ul), and 3 ul of the diluted T7

DNA polymerase (0.5 units per ul). The reaction was incubated at 37° C. for 3 hours, followed by heat inactivation at 68° C. for 10 minutes. Two ul of the SDM reaction mixture were used to transfect *E. coli* DHα-5 competent cells.

For the 5' half clone, pFIV5'-D-11, incorporation of one of the mutagenesis oligonucleotides, PF-5, resulted in an addition of a Hinc II site. A preliminary screening with Hinc II resulted in the identification of four positive mutants that were designated as pFIV5'-D-11/M-4, pFIV5'-D-11/M-22, pFIV5'-D-11/M-28 and pFIV5'-D-11/M-52. These four mutants were completely sequenced to verify the incorporation of the other seven desired mutations. The sequencing results revealed that three of the four clones contained all eight mutations. One clone, pFIV5'-D-11/M-28, had only seven positions that were mutated.

Clone pFIV5'-D-11/M-52 was selected as the 5' half clone to be used to construct the full length FIV-141 clone. For the 3' half clone, pFIV3'-2-A-1$^+$, preliminary screening with BspH I digestion identified 10 mutants in which a BspH I restriction site was eliminated due to the incorporation of the mutagenesis oligonucleotide pF13. Complete sequencing revealed that 8 of the 10 clones contained mutations at all seven desired positions. One of the mutants, "pFIV3'-2-A-1$^+$/M-21," contained all of the 8 changes and was selected to be used as the 3' half clone in constructing the full length FIV-141 clone.

Construction of the Full Length FIV-141 Clone

In order to construct the full length FIV-141 clone, a 5.5 kb MluI/XhoI fragment derived from the 5' half clone, pFIV 5'-D-11/M-52, was ligated to the 3' half clone pFIV3'-2-A-1$^+$/M-21, which had been digested with the same two restriction enzymes. The full length ligation product was screened by PCR amplification using a forward primer directed to the 5' half clone and a reverse primer directed to the 3' half clone. The forward primer, pr-9, had the sequence: 5'-(5147)-TTAAAGGATGAAGAGAAGGGATATTTT-CTT-(5176)-3' (SEQ ID NO:10). The reverse primer, pr-10, had the sequence: 5'-(5631)-TTTCAA-TATCATCCCACATAAATC- CTGT-(5604) 3', (SEQ ID NO:9). Positive clones were confirmed by restriction digestion and sequencing. One of the resulting full length clones was designated as "pFIV-141-B1" and selected for characterization both in vitro and in vivo.

Example 2

Demonstration that the Full Length Molecular Clone is Infectious

Transfection

Crandell feline kidney (CRFK) cells were grown in six well plates to a confluency of 40 to 60%. Transfection was accomplished by introducing 2 ug of plasmid DNA and following the basic protocol recommended by Trans IT Polyamine Transfection Reagents (Mirus, Madison, Wis.). Briefly, 10 ul of TransIT Lt-1 (Panvera) was mixed with 1 ml RPMI 1640 medium and incubated at room temperature for 15 minutes. Two ug of plasmid DNA was added to the RPMI/Lt-1 solution and incubated for another 15 minutes at room temperature. Media was removed from wells, cells were washed once with PBS, and the DNA cocktails were added to the cell monolayers. After incubation at 37° C. in a $CO_2$ incubator for four hours, the DNA cocktails were removed from the wells and 2 ml of RPMI 1650 medium supplemented with 3% fetal serum (FS) was added to each well. Twenty-four hours post-transfection, cell supernatants were assayed for FIV production, reverse transcriptase (RT) activity and viral infectivity.

FIV Production from Transfected CRFK Cells

Supernatants from the transfected CRFK cells were harvested on a daily basis after the transfection, and were assayed for FIV capsid protein production using the FIV Antigen Test Kit (IDEXX, Portland, Me.), according to the protocol recommended by the manufacturer. This enzyme immunoassay was designed to detect the predominant group-associated antigen of FIV p26 capsid protein. FIV antigen p26 was detected at 24 hours post-transfection (PT), reached a peak at 72 hours PT, and then decreased to background levels at 11 days PT (see FIG. 1).

In order to confirm virus production from the transfected (CRFK) cells, a reverse transcriptase (RT) activity assay (Boehringer Mannheim, Indianapolis, Ind.) was performed to detect virion-associated RT activity in the transfected cell supernatants. Briefly, 200 ul of cell supernatant was harvested and spun 5 minutes in a microfuge to pellet cells and cell debris. Supernatants were centrifuged at 20,000 g for 20 minutes at 4° C. in a swinging bucket rotor to pellet FIV virus particles. Viral particle pellets were resuspended in 40 ul of lysis buffer from the kit, and assays were then performed as recommended by the manufacturer. Virus production from transfected cells was demonstrated in cell supernatants 48 hours post-transfection (PT).

Infection of CRFK Cells

FIV-141 wild type virus does not infect CRFK cells. In order to determine whether the molecular clone virus exhibits similar behavior, CRFK cells were grown in 6 well plates and inoculated with 200 ul of p26+ conditioned medium from transfected CRFK cells. After incubation for 2 hours at 37° C., cells were washed once with PBS, and 2 ml of RPMI 1640 medium supplemented with 3% FS was added to each well. Supernatants were then monitored for virus production by FIV p26 ELISA every 3 to 4 days post-transfection. It was found that, similar to the wild type virus, the FIV-141 clone does not infect CRFK cells.

Infection of FeP2 Cells by Co-Culture with Transfected CRFK Cells

CRFK cells were grown in 6 well plates and transfected as described above. At 48 hours post-transfection, $2 \times 10^6$ FeP2 cells were added to each p26+ transfected well. After co-culture of cells for 72 hours, FeP2 cells (nonadherent) were separated from CRFK cells (adherent). The supernatants from the FeP2 cells were harvested and monitored for virus production by FIV p26 ELISA every 3 to 4 days. Four days post co-cultivation, high levels of virus production were demonstrated in the FeP2 cell supernatants (see FIG. 2). Virus titer reached a plateau 6 days post-transfection, indicating that the FIV-141 molecular clone virus is infectious in FeP2 cells. The results also suggested that infection of CRFK cells is blocked in an early stage of virus infection, i.e, at the time of the entry of virus into cells.

Overall, it was concluded that, upon transfection into CRFK cells, the FIV-141 molecular clone can replicate in the cell, and virus particles released from the cells are infectious for FeP2 T lymphocytes.

Infection of FeP2 Cells by Adsorption

Figure 2:
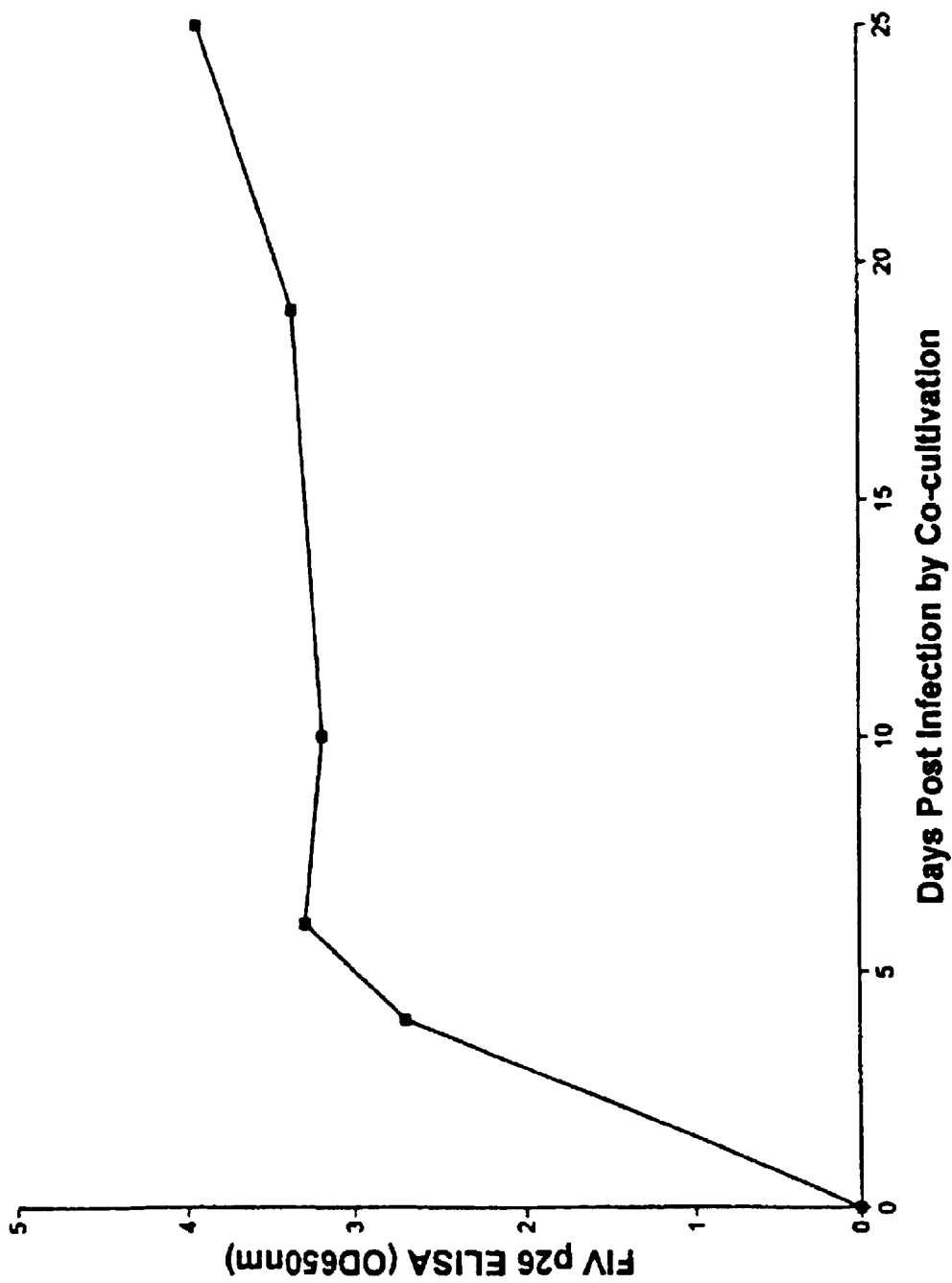
FIG. 2: Infection of FeP2 T Lymphocytes by Co-culture. CRFK cells were grown in six well plates and transfected with plasmid DNA encoding the full length FIV-141 genome. Forty-eight hours after transfection, $2 \times 10^6$ FeP2 cells were introduced into each well. Beginning 72 hours after co-cultivation, FeP2 cells were separated and their supernatants were tested for the presence of FIV p26 capsid protein by ELISA.
Figure 3:
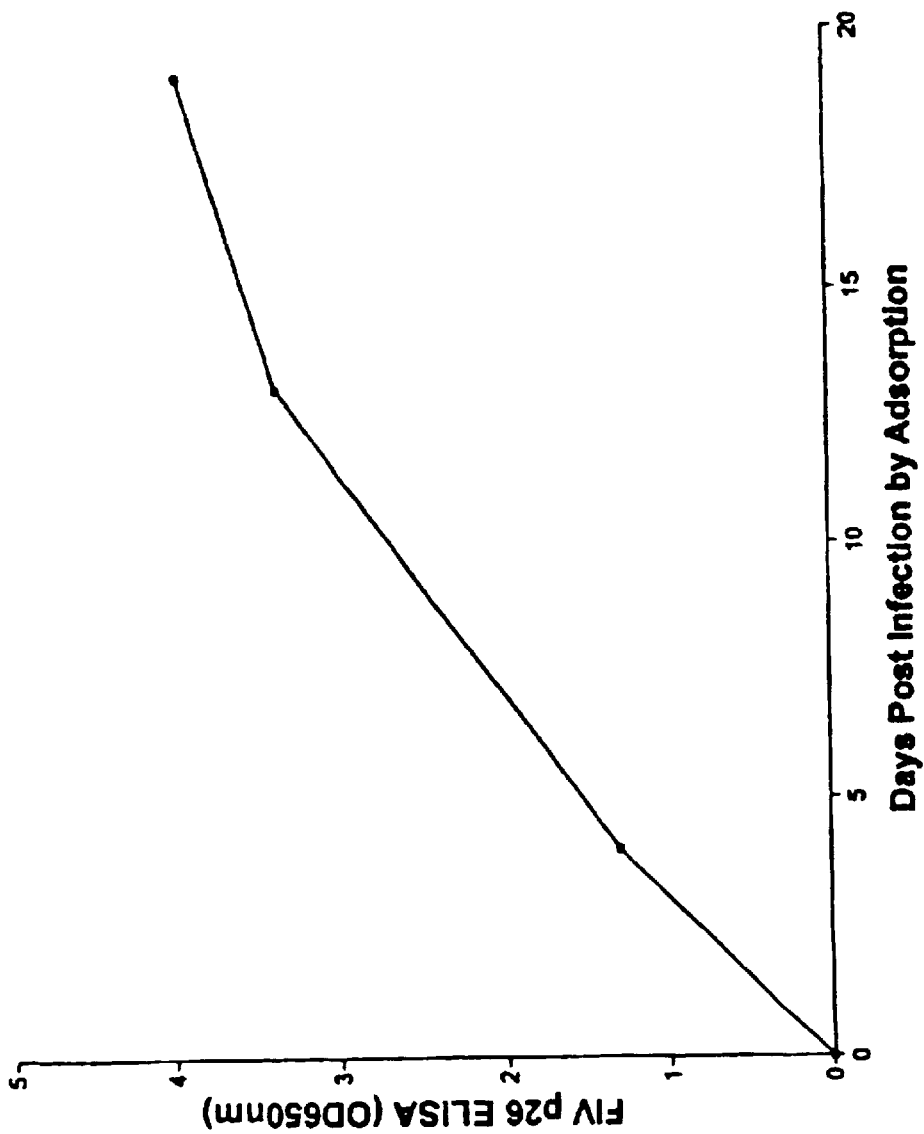
FIG. 3: Infection of FeP2 Cells by Adsorption. $2 \times 10^6$ FeP2 cells were suspended in 200 ul of FIV-141 virus-containing conditioned medium derived from CRFK cells transfected with the full length infectious FIV-141 clone. Beginning at four days post-infection, FeP2 cell supernatants were tested for the presence of FIV-141 virus using a p26 ELISA assay.

FeP2 cells ($2 \times 10^6$) were suspended in 200 ul of p26+ conditioned medium obtained from transfected CRFK cells and incubated at 37° C. for two hours. Cells were washed with PBS, suspended in 2 ml Opti-MEM medium supplemented with 10% heat inactivated FCS, and incubated at 37° C. Supernatants were harvested and monitored for virus production by FIV p26 ELISA every three to four days. Four days post-infection, virus release from infected FeP2 cells was detected in the supernatants and reached a peak by three weeks post-infection (FIG. 3). The results indicate that productive infection of FeP2 cells by FIV-141 can be achieved through either adsorption or co-culture with transfected CRFK cells. Compared to infection by co-cultivation, virus production reached a plateau much more slowly when infection took place by adsorption (FIGS. 2 and 3).

Example 3
Mutant FIV-141 Clones and Their Use in Vaccines

In order to develop FIV-141 vaccine candidates, the infectious FIV-141 wild-type clone was used to construct a number of gene-deleted clones. The general criteria for making the mutant clones are:

1. The deletions or mutations introduced into the FIV-141 genome must be severe enough so that virus infectivity is substantially reduced (attenuated) after the clones are transfected into cultured cells in vitro or administered to cats in vivo.
2. The deletions or mutations introduced into the FIV-141 genome should not abolish the replication competency of the viral genome, or the ability to express viral proteins at high levels.

Other factors to be considered are whether the gene-deleted genome will integrate into host chromosomes, whether defective virus particles will form, and the level of viral structural proteins that will be expressed. Based upon these considerations, a number of genes and elements were targeted for deletion. Because viral genome replication was to be maintained, neither the RT nor PR genes of FIV-141 were mutated.

A. Deletions in the Gag Region

The Gag polyprotein contains three virion structural proteins, MA, CA and NC. Three gene-deletion clones were constructed with a deletion in each of these proteins.

MA del Mutation

Site-directed mutagenesis was performed to create two Spe I restriction sites in the C-terminal portion of the MA protein using the 5' half clone pFIV5'-D-11/M-52 as template and the mutagenesis primers: Mpma-1 (5'-AGTAAAGAAATTGACATGGCGATTACTAGTTTAAA-AGTTTTTGCAGTGGC-3', (SEQ ID NO:32); and Mpma-2 (5'-CCATCTATAAAAGAAAGTGGGACTAGTGAAG AAGGACCTCCACAGGC-3', SEQ ID NO:33).

The Spe I sites introduced by the primers are underlined in the sequences. SDM was performed as discussed previously in order to repair the putative errors in the 5' and 3' half clones. Mutants were screened by Spe I restriction digestion and positive clones were used to construct the deletion clone. Spe I digestion was performed to release the Spe I fragment and the remaining part of the clone was self ligated to create the deletion clones. These were screened by PCR amplification using primer sets flanking the deleted region and confirmation was obtained by nucleotide sequencing. The 5' half clone with the deletion was ligated to the 3' half clone pFIV3'-2A-1+/M-21 to generate the full length clone with the deletion. This clone was named FIV-141 MA deletion clone and contained a deletion of 123 bases from nucleotide 879 to nucleotide 1001, corresponding to 41 amino acids from residues 85 to 125 at the C-terminus of MA.

CA del Mutation

SDM was performed to create two Spe I sites in the CA region of FIV-141 using the 5' half clone pFIV5'-D-11/M-52 as template and, as primers, Mpca-1 (5'-ATTCAAACAGTAAATGGAGCAACTAGTTATGTAGC-CCTTGATCCAAAAATG-3', SEQ ID NO:34) and Mpca-2 (5'-ACAGCCTTTTCAGCTAATTTAACTAGTACTGAT-ATGGCTACATTAATTATG-3', SEQ ID NO:35). After deletion of the Spe I restriction fragment, the 5' half clone was ligated to pFIV3'-2A-1+/M-21 to generate the gene-deleted full length clone. This clone has a 114 base pair deletion from nucleotides 1056 to 1169, corresponding to the 38 amino acids from positions 9 to 46 at the N-terminus of the CA protein.

NC del Mutation

The 5' half clone has unique Sca I and Sma I sites at nucleotides 1635 and 1876 respectively. The clone was digested with Sca I and Sma I to release a 242 base pair fragment. The remaining portion of the 5' half clone was self-ligated and then joined to the 3' half clone to generate the gene-deleted full length clone. The deletion consists of 63 bases (21 amino acid residues) in the CA region, 27 bases (9 amino acid residues) between the CA and NC protein and 152 bases (51 amino acid residues) at the N-terminal portion of the NC protein. The deletion also caused a −1 reading frame shift and, therefore, the C-terminal portion of the NC protein cannot be expressed by this clone.

B. Deletions in the ENV Region

The ENV precursor glycoprotein is processed into two mature proteins: SU and TM. Six deletion clones were constructed in the ENV region.

ENV del Mutation

SDM was performed to create two BstE II sites in the ENV region using the 3' half clone pFIV3'-2A-1+/M-21 as template and, as mutagenesis primers, Mpenv-1 (5'-ACTATAGTCTATTTACT ACTATAGTCTATTTAC-TAACTGGTTACCTGAGATATTTAATAAGCCATAG-3', NO:36) and Mpenv-2 (5'-TACTTATATGCTTGCCTA-CATTGGGTTACCGTATAAGAAACTGTACTA ATAAA-A- 3', SEQ ID NO:37). The BstE II sites in the primer are underlined. After deletion of the BstE II fragment, the self-ligated clone was joined to pFIV5'-D-11/M-52. The resulting clone has a deletion of 2103 bases from nucleotides 6577 to 8679, corresponding to the middle 701 amino acids of the ENV protein (residues 106 to 806). The N-terminal 105 residues, the majority of which overlaps the first exon of the Rev protein, and the C-terminal 45 residues which overlaps with the Rev responsible element (RRE), were maintained in the deletion clone.

SU del Mutation

Two Spe I sites were generated in the SU region of FIV-141 by SDM using clone pFIV3'-2A-1+/M-21 as template and, as mutagenesis primers, Mpsu-1 (5'-GAGGTATAAAGGTAAACAAAAAACTAGT GCCATTCATATTATGTTAGCCCTTGC-3', SEQ ID NO:38) and Mpsu-2 (5'-ACTAACTAT- AGTCTATTTAC-TAACAACTAGT TTGAGATATTTAATAAGCCATA-GAAAC-3', SEQ ID NO:39). The Spe I fragment was deleted by Spe I digestion followed by self ligation of the large remaining fragment. The resulting clone was ligated to pFIV5'-D-11/M-52. This clone has a deletion of 1509 basis from nucleotides 6577 to 8085, corresponding to a deletion of 503 amino acids (residues 106 to 608) of the SU protein. The clone maintains the N-terminal 105 amino acids of the SU protein.

V3/4 del Mutation

SDM was performed to create two Sph I sites flanking the V3 and V4 region of the SU protein. The clone pFIV3'-2A-1+/M-21 was used as template along with the mutagenesis primers: Mpenv-5 (5'-

ATACCGAAATGTGGATGGTGGAATCAGGCATGC-TATTATAATAATTGTAAATGGGAAGAAGC-3', SEQ ID NO:40) and Mpenv6 (5'-GCACTAT- GTACAATTGTTC-CTTACAGGCATGCTTCACTATGAAAATAGAGG-ACCTTAT3', SEQ ID NO:41). Sph I sites are underlined. After digestion to remove the Sph I fragment, the clone was self-ligated and then joined to pFIV5'-D-11/M-52. This clone contains a deletion of 432 bases from position 7339 to 7770, corresponding to a deletion of 144 amino acids (from residue 360 to 503) of the SU protein, covering the V3 and V4 regions.

V7/8 del Mutation

SDM was used to create two Sph I sites flanking the V7 and V8 region of the TM protein. This was accomplished using the clone pFIV3'-2A-1$^+$/M-21 as template and the mutagenesis primers Mpenv-7 (5'-GAATCAATT-CTTTTGTAAGATCGCATGCAATCTGTGGACAATGTA-TAACATGACTA-3', SEQ ID NO:42) and Mpenv-8 (5'-GGGAAAATTGGGTGGGATGGATAGGTAAGATCGCA-TGCTATTTAAAAGGACTTCTTGGTAG-3', SEQ.ID NO:43). Sph I sites are underlined. Digestion with Sph I resulted in the elimination of 216 bases from nucleotides 8380 to 8595, and was followed by ligation of the large fragment. The resulting clone was then joined to the 5' half clone pFIV5'-D-11/M-52 to generate "V7/8del." This contains the deletion of 72 amino acids (from residues 98 to 169) of the TM protein covering the V7 and V8 various regions.

TMf del Mutation

The 3' half clone of FIV-141 has a unique Age I site at nucleotide 8145. SDM was performed to create a second Age I site at position 8071. The 3' half clone was used as template along with the mutagenesis primer, Mpenv-3 (5'-GGAAGAAGTTATGAGGTATACCGGTAAACAAA-AAGGGCC-3', SEQ ID NO:44). A 75-base fragment between the two Age I sites was deleted by restriction enzyme digestion followed by self-ligation of the large restriction fragment. The resulting clone was ligated to the 5' half clone to generate "TMf del." This contains a deletion of 25 amino acids in the cleavage junction between the SU and TM proteins. The deleted amino acids include 6 C-terminal residues of the SU protein (4 of which are basic (either K or R) and required for the processing of the SU/TM cleavage site) and 19 N-terminal residues of the fusion peptide of the TM protein (required for membrane fusion between virion envelope and cell membrane).

CT del Mutation

SDM was performed to truncate the cytoplasmic tail of the TM protein using the 3' half clone pFIV3'-2A-1$^+$/M-21 as template and the mutagenesis primer, Mpenv4 (5'-CTACTTATATGCTTGCCTACATTGGTCGACTGA-TAGTGAAACTGTACTAATAAAATATTGGG-3', SEQ ID NO:45). A Sal I restriction site (underlined) was incorporated into the oligonucleotides by silent mutation to facilitate the screening of mutants. Three tandemly repeated translation stop codons (italicized) were incorporated in the primer right after the transmembrane domain of the TM protein. The resulting clone was ligated to the 5' half clone to generate "CT del." This has a 138-base truncation from nucleotides 8686 to 8823 (corresponding to a truncation of 46 amino acids from the cytoplasmic domain of the TM protein).

C. Deletions in the Pol Region

The Pol polyprotein consists of four enzymatic proteins: PR, RT, DU, and IN. Two deletion clones were constructed in the Pol region.

DU del Mutation

SDM was performed to create two Spe I sites in the DU region using the 5' half clone pFIV5'-D-11/M-52 as template and, as mutagenesis primers, Mpdu-1 (5'-GATGGTTATAGAAGGTGAAGGAATTACTAGT- AAA-AGATCAGAAGATGCAGGATATG-3', SEQ ID NO: 46) and Mpdu-2 (5'-GAAATAATAATGGATTCAGA-AAGAGGAACTAGTGGATTTGGGTCAACTGGA GTCTTTTC-3', SEQ ID NO:47). Spe I sites in the primers are underlined. A deletion of 345 bases from nucleotide 4019 to 4363 was achieved by Spe I digestion followed by self-ligation of the large restriction fragment. The resulting clone was joined to the clone pFIV3'-2A-1$^+$/M-21 to generate "DU del." The clone contains a deletion of 115 amino acids corresponding to almost the entire DU protein.

IN del Mutation

Two Spe I sites were created by SDM in the IN region of FIV-141 using pFIV5'-D-11/M-52 as template and the mutagenesis oligonucleotides, Mpin-1 (5'-CTTCATGGGTGGACAGAATTGAAACTAGTGT-ATTAAATCATGAAAAATTTCACTCAG-3', SEQ ID NO:48) and Mpin-2 (5'-GCAATGGG- TGTATTATAAA-GATCAGACTAGTAAAAAGTGGAAGGGACCAATGA-GAGTAG-3', SEQ ID NO:49). Spe I sites in the primers are underlined. After deletion of the Spe I fragment and self ligation, the resulting clone was joined with pFIV3'-2A-1$^+$/M-21 to generate "IN del." This contains a deletion of 669 bases from nucleotide 4418 to 5036 corresponding to almost the entire IN protein (223 amino acids, from residue 9 to 231 of IN).

D. Deletions in Regulatory Genes or Elements

Three regulatory proteins identified in FIV are Rev, Vif and ORF2. A Rev-responsible element has been reported at the 3' end of the FIV genome. Five deletion clones were constructed in these regions.

Vifn del Mutation

A unique Mlu I site was introduced in the middle of the Vif gene in the 5' half clone pFIV 5'-D-11/M-52. SDM was performed to create a second Mlu I site at the N-terminus of the Vif gene using pFIV3'-D-11/M-52 as template and the mutagenesis primer, Mpvif-1 (5'-AGAAGACTCTTTGCAGTTCTCCAATGAACGCGT-TAGAGTGCCATGTTATACATATCG-3', SEQ ID NO:50). The Mlu I site in the primer is underlined. A restriction fragment of 150 bases from nucleotide 5286 to 5435 was deleted by Mlu I digestion followed by self ligation of the large fragment. The resulting deletion clone was joined to pFIV3'-2A-1$^+$/M-21 to generate "Vifn del." This contains a deletion of 50 amino acids (from residue 19 to 68) at the N-terminal portion of the Vif protein.

Vifc del Mutation

The 3' half clone pFIV3'-2A-1$^+$/M-21 has a unique Mlu I site within the Vif region. A second Mlu I site was created by SDM at the C-terminus of the Vif protein using pFIV3'-2A-1$^+$/M-21 as template and the mutagenesis primer Mpvif-2 (5'-CGTGTGGCAAAGAGGCTAAA ACGCGTAGAGGCTGTTGTAATCAG-3', SEQ ID NO:51). The Mlu I site in the primer is underlined. After deletion of the Mlu I fragment, the resulting clone was ligated to the 5' half clone pFIV5'-D-11/M-52 to generate "Vifc del." This contains a deletion of 438 bases from nucleotide 5436 to 5873, corresponding to a deletion of 146 amino acids (from residue 69 to 214) at the C-terminal portion of the Vif protein.

Vif del Mutation

To construct "Vif del," the Xho I/Mlu I restriction fragment of Vifc del was replaced with a 5.3 kb Xho I/Mlu I fragment of Vifn del. The resulting clone contains a deletion of 588 bases from nucleotide 5286 to 5873, corresponding to a deletion of 196 amino acids (from residue 19 to 214), almost the entire Vif protein.

ORF(2) del Mutation

Two Mlu I sites were created by SDM at nucleotides 5988 and 6224 (at the N- and C-termini of ORF(2)). This was accomplished using pFIV3'-2A-1+/M-21 as template and, as mutagenesis primers, Mporf-1 (5'-GTGGAC-GGGAGAATTATGA<u>ACGCGT</u>GAA CTAATCCCAC-TGTTTAATAAGGTTACAG-3', SEQ ID NO:52) and Mporf-2 (5'-CTACATTATCCAT- AAATACTGCCTAG <u>ACGCGT</u>TTTCTTTTAATATTTCATCT- GCAG-3', SEQ ID NO: 53). Mlu I sites in the primers are underlined. In addition to the two Mlu I sites created by SDM, there is an Mlu I site at nucleotide 5436 in the clone. To construct "ORF(2) del," a 5.4 kb Mlu I/Xho I fragment from the 5' half clone pFIV5'-D-11/M-52 was ligated to the large Mlu I/Xho I fragment of the 3' half clone pFIV3'-2A-1+/M-21. A 552 base Mlu I fragment from position 5436 to 5988 was then inserted into the resulting clone. ORF(2) del contains a deletion of 237 bases, covering the entire ORF(2) gene.

RRE del Mutation

SDM was performed to create two Spe I sites in the RRE region using pFIV3'-2A-1+/M-21 as template and the mutagenesis primers, Mprre-1 (5'-GGCAT- ATCT-GAAAAAGAGGAGGAATGA<u>ACTAGT</u>ATATCAGACC-TGTAGAATACA-3', SEQ ID NO:54) and Mprre-2 (5'-GAGGAGGATGTGTCATATGAATCAAAT<u>ACTAGT</u>-CAAAAATAACAGTAAAATCTATATTG-3', SEQ ID NO:55). Spe I sites in the primers are underlined. Deletion of the Spe I fragment was achieved by Spe I digestion followed by self ligation of the large fragment. The resulting deletion clone was ligated to pFIV5'-D-11/M-52 to generate "RRE del." This contains a deletion of 84 bases from nucleotide 8827 to 8910.

E. Double Deletions

FIV-141 MA del clone was digested with Xho I and BstE II, and a 4.8 kb DNA fragment containing the first half of the FIV-141 genome was purified and used for the construction of the three double deletion clones, MA del/TMf del, MA del/V3/4 del, and MA del/Vif del, as follows.

MA del/Tmf del Mutation

FIV-141 Tmf del clone was digested with the same two restriction enzymes and a 7.8 kb fragment, which contains the second half of the FIV-141, was isolated and purified. Ligation of the 4.8 kb and 7.8 kb fragments resulted in a double deletion clone, i.e., FIV-141 MA del/Tmf del, which consists of deletions of 41 amino acids at the C-terminus of the MA and 25 amino acids in the fusion peptide of TM.

MA del/V3/4 del Mutation

FIV-141 V3/4 del clone was digested with Xho I and BstE II, and a 7.8 kb fragment comprising the second half of the FIV-141 genome was purified and ligated to the 4.8 kb fragment derived from the FIV-141 MA del clone. The resulting double deletion clone, i e., FIV-141 MA del/V3/4 del, contains a deletion of 41 amino acids at the C-terminus of MA and a deletion of 144 amino acids of the V3 and V4 regions within the ENV.

MA del/Vif del Mutation

FIV-141 Vif del clone was digested with Xho I and BstE II and a 7.8 kb fragment containing the second half of the genome was purified and ligated to the same 4.8 kb fragment derived from the FIV-141 MA del clone. The resulting double deletion clone, i.e., FIV-141 MA del/Vif del, has a deletion of 41 amino acids at the C-terminus of MA and a deletion of 196 amino acids of Vif.

ENV del/IN del Mutation

Plasmid DNA comprising the FIV-141 ENV del clone prepared as above was digested with Mlu I and Sal I, and a 2 kb fragment containing the second half of the FIV-141 genome with a deletion of 2.1 kb of the ENV gene was isolated and purified. FIV-141 IN del clone prepared as above was digested with the same two restriction enzymes, and a 4.7 kb fragment consisting of the first half of the FIV-141 genome with a deletion of the IN gene was purified. The two fragments were ligated and cloned into the pCR-Script Amp SK(+) vector. The resulting double deletion clone, FIV-141 ENV del/IN del, contains a deletion of 2103 bases in the ENV gene and a deletion of 669 bases in the IN gene.

Example 4:

Characterization of the FIV-141 Gene Deletion Clones

A. Viral Protein Expression and/or Defective Virus Production

Figure 4:
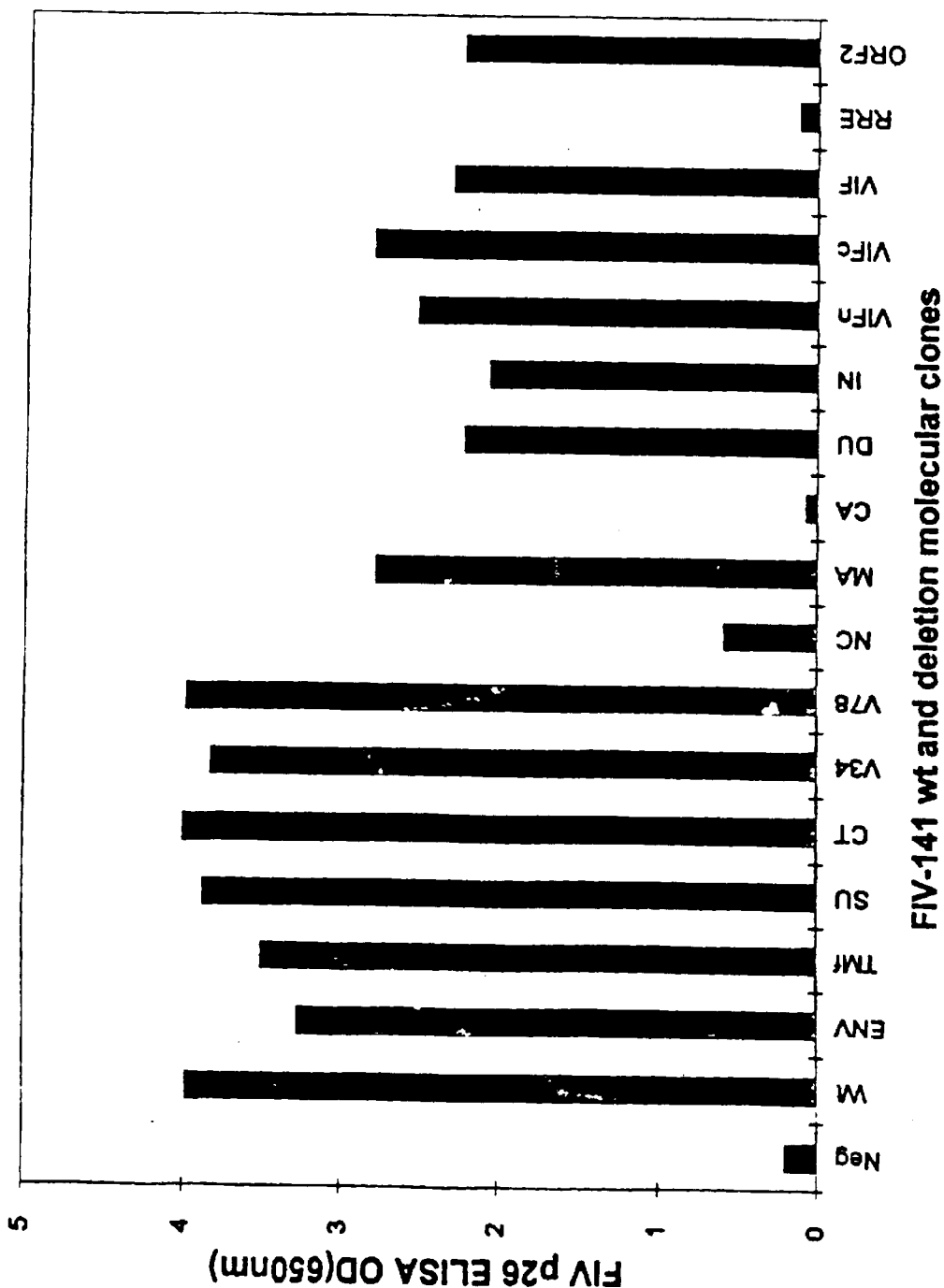
FIG. 4: Expression of FIV-141 Viral Protein by Deletion Clones. A variety of clones mutated to delete FIV genes or regulatory regions were made and transfected into CRFK cells. After 48 hours, cell supernatants were assayed for the presence of FIV p26 capsid protein by ELISA. The results for each deletion clone, as well as the wild type FIV-141 molecular clone, are shown.

Each plasmid of the deletion clones was transfected into CRFK cells as previously described. FIV p26 ELISA assays were performed to detect viral protein expression and/or virus particle production in the transfected cell supernatants. At 48 hours post-transfection, samples from 13 of the constructs were found to produce a strong positive signal comparable to that observed for the wild type FIV-141 molecular clone (see FIG. 4). The highest levels of virus particle production were observed for the six deletion clones in the ENV region, including ENV del, TMf del, SU del, CT del, V3/4 del and V7/8 del.

Comparable levels of virus particle production were obtained for seven other deletion clones, including three deletion clones in the Vif region (Vifn del, Vifc del and Vif del), MA del, DU del, IN del and ORF(2) del. The results indicate that the deletions carried by these 13 clones do not interfere with the formation and release of virus particles from the transfected cells. A relatively weak positive signal was detected for NC del, indicating that deletion in this region affects virus particle assembly or release.

No virus particle production was detected in the supernatants of cells transfected with CA del or with RRE del. The deletion in the C-terminus of the CA protein may either abolish virus particle formation or result in loss of the epitope recognized by the monoclonal antibody (MAb) used in the p26 ELISA kit. As expected, deletion in the RRE region resulted in a block of the export of unspliced viral RNA from the nucleus to the cytoplasm, leading to either a total lack of, or a dramatic decrease in, the expression of viral structural proteins.

B. Intracellular RT-PCR to Detect Viral RNA Expression

Intracellular RT-PCR was performed to detect viral RNA expression in the two deletion clones, CA del and RRE del. Plasmid DNA for each clone was transfected into different CRFK cells. Forty-eight hours after transfection, total RNA was isolated from the transfected cells using an RNeasy kit (Qiagen, Chatsworth, Calif.). The RNA was eluted in 50 ul of DEPC water, and 2 ul of each RNA sample was used to synthesize the first strand of cDNA using Superscript II (Gibco BRL, Gaithersburg, Md.).

A 585 base pair fragment from nucleotides 2958 to 3542 was amplified using as a forward primer Sp-8 (5'-TATTATGGTGGGGATTTGAAAC-3', SEQ ID NO:56) and, as a reverse primer, Sp-20 (5'-TAATTAGATTTGATTCCCAGGC-3', SEQ ID NO:57). Two ul of cDNA from each reaction and, as a control, 2 ul of total RNA from each preparation, were used as the template in PCR reactions. Each reaction was performed in a volume of 100 ul using a PCR amplification kit (Gibco BRL, Gaithersburg). The reaction proceeded as follows: 25 cycles at 94° C. for 30 seconds; 55° C. for 30 seconds; and 72° C. for another 30 seconds. Ten ul from each reaction was loaded on a 1% agarose gel. A specific band with the expected size was observed for both CA del and RRE del clones, indicating that viral RNA expression occurred in the cells transfected with these clones. The results suggest that the failure to detect p26 protein expression by ELISA for CA del is probably due to either a failure of virus particle formation or a lack of the epitope recognized by the antibody used in the p26 ELISA assay. For the RRE deletion clone, viral gene expression was demonstrated by intracellular RT-PCR, but no p26 protein expression was detected using the ELISA assay. The discrepancy may reflect a much higher sensitivity of RT-PCR assay when compared to the ELISA.

C. Encapsidation of Viral Genome and RT Enzyme in the Defective Virus Particles

Transfection of CRFK cells by the majority of the FIV-141 deletion clones resulted in the production and release of defective virus particles. In order to determine whether gene-deleted viral genomes and RT protein were encapsidated into virus particles, virion-associated RT PCR and RT activity assays were performed. Briefly, 48 hours post-transfection, 200 ul of the supernatant from each transfected CRFK culture were harvested and spun 5 minutes in a microfuge to pellet cells and cellular debris. The virus particles in the supernatants were pelleted by ultracentrifugation at 20,000 g for 20 minutes at 4° C. in a swinging bucket rotor. To test for encapsidation, virus pellets were resuspended in 350 ul RLT buffer from the RNeasy kit, and viral RNA was purified by elution in 50 ul DEPC water as recommended by the manufacturer. First strand cDNA was made using Superscript II, and PCR amplification was performed as described previously using the Sp-8 and Sp-20 primer set.

Fourteen of 16 deletion clones showed a specific band after RT-PCR amplification, indicating that transfection of CRFK cells by these clones produced defective virus particles and that the gene-deleted viral genomes were encapsidated. The 14 clones consisted of 6 clones from the ENV region (including ENV del, TMf del, SU del, CT del, V3/4 del, and V7/8 del); 3 clones from the Vif region (Vifn del, Vifc del, and Vif del); 2 clones from the Pol region (DU del and IN del); 2 clones from the regulatory gene/element region (ORF(2) del and RRE del); and 1 clone from the Gag region (MA del). Consistent with the p26 ELISA data, CA del showed a negative signal in the virion-associated RT-PCR assay. The NC protein is required for the packaging of the viral genome into the virion and, as expected, no virion-associated gene-deleted viral RNA genome was detected by RT-PCR for NC del. For RRE del, virion-associated gene-deleted viral RNA was demonstrated to be present but no virus particle production was detected using the p26 ELISA assay. The discrepancy in these results may again reflect a much higher sensitivity of the RT-PCR assay relative to the ELISA.

For testing encapsidation of the RT (i.e. reverse transcriptase) enzyme in defective virus particles, virus pellets were resuspended in 40 ul of the lysis buffer from the RT ELISA kit, and the assay was allowed to proceed as recommended by the manufacturer. Consistent with data obtained using p26 ELISA assays and virion-associated RT-PCR assays, virion-associated RT activity could be detected for 14 deletion clones, including ENV del; SU del; TMf del; V3/4 del; V7/8 del; CT del; MA del; DU del; IN del; Vifn del; Vifc del; Vif del; ORF(2) del; and NC del. No virion-associated RT activity was detected in the CA or RRE deletion clones.

D. Infectivity of the FIV-141 Gene-Deleted Clones In Vitro

CRFK cells were grown in six well plates and transfected as described previously. Forty-eight hours after transfection, $2 \times 10^6$ FeP2 cells were added to each well. After co-cultivation of the cells for 72 hours, FeP2 cells were separated from CRFK cells and the supernatants from FeP2 cell cultures were harvested and monitored for virus production using the FIV p26 ELISA assay every 3 to 4 days for a total of 4 to 6 weeks.

Figure 5:
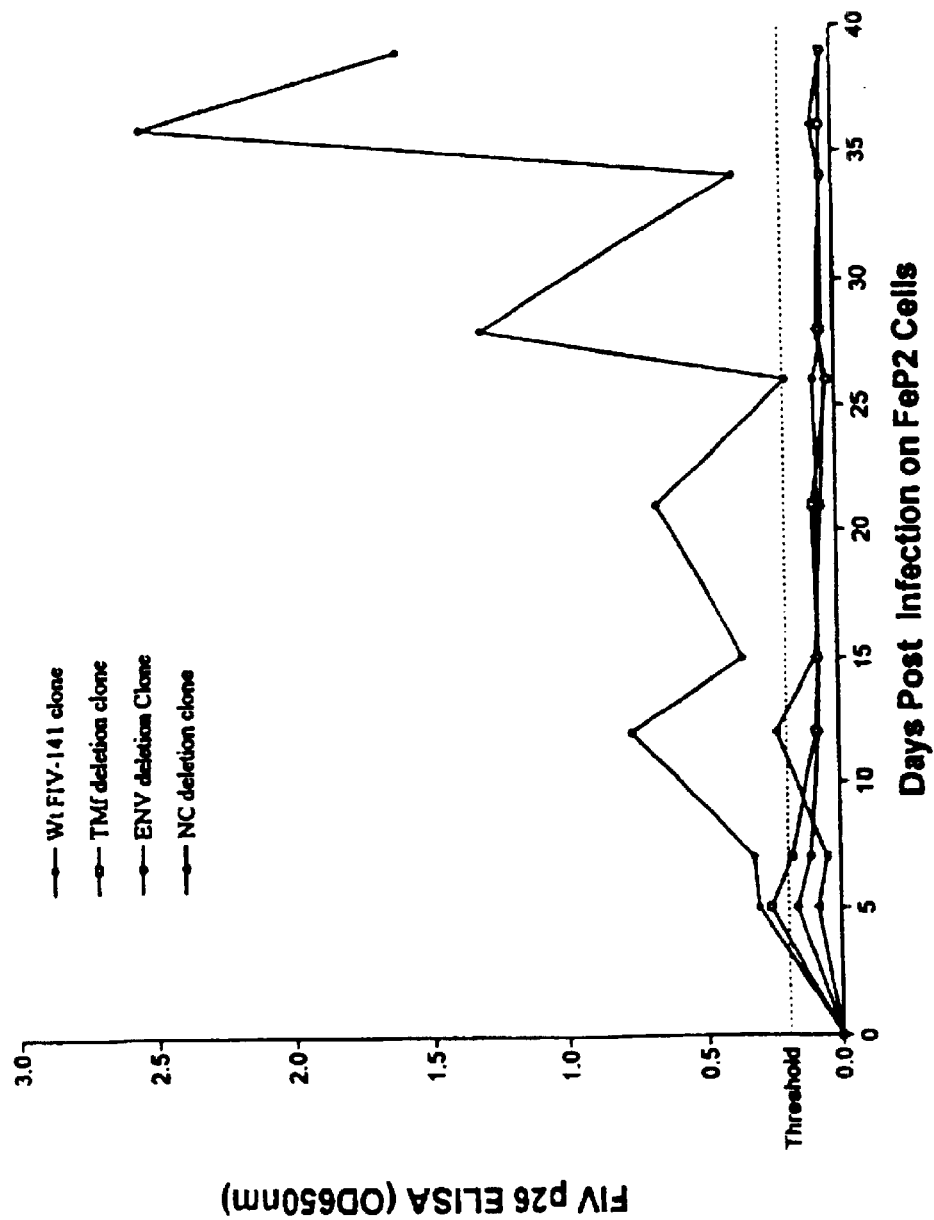
FIGS. 5–10: Infection of FeP2 T Lymphocytes by FIV-141 Mutants. CRFK cells were grown in six well plates and infected with one of three different FIV-141 deletion clones: TMf del, ENV del, or NC del. After 48 hours, FeP2 cells were added to each well and co-cultures were maintained for an additional 72 hours. The FeP2 cells were then separated from the CRFK cells and assayed for the presence of p26 antigen using an ELISA assay. Monitoring of p26 levels was repeated every 3–4 days and results are shown in FIG. 5. The experiment was repeated using: Vifn del, Vifc del and Vif del (FIG. 6); MA del and CA del (FIG. 7); V3/4 del, V7/8 del and CT del (FIG. 8); ORF(2) del (FIG. 9); and DU del, SU del, IN del, and RRE del (FIG. 10).
Figure 6:
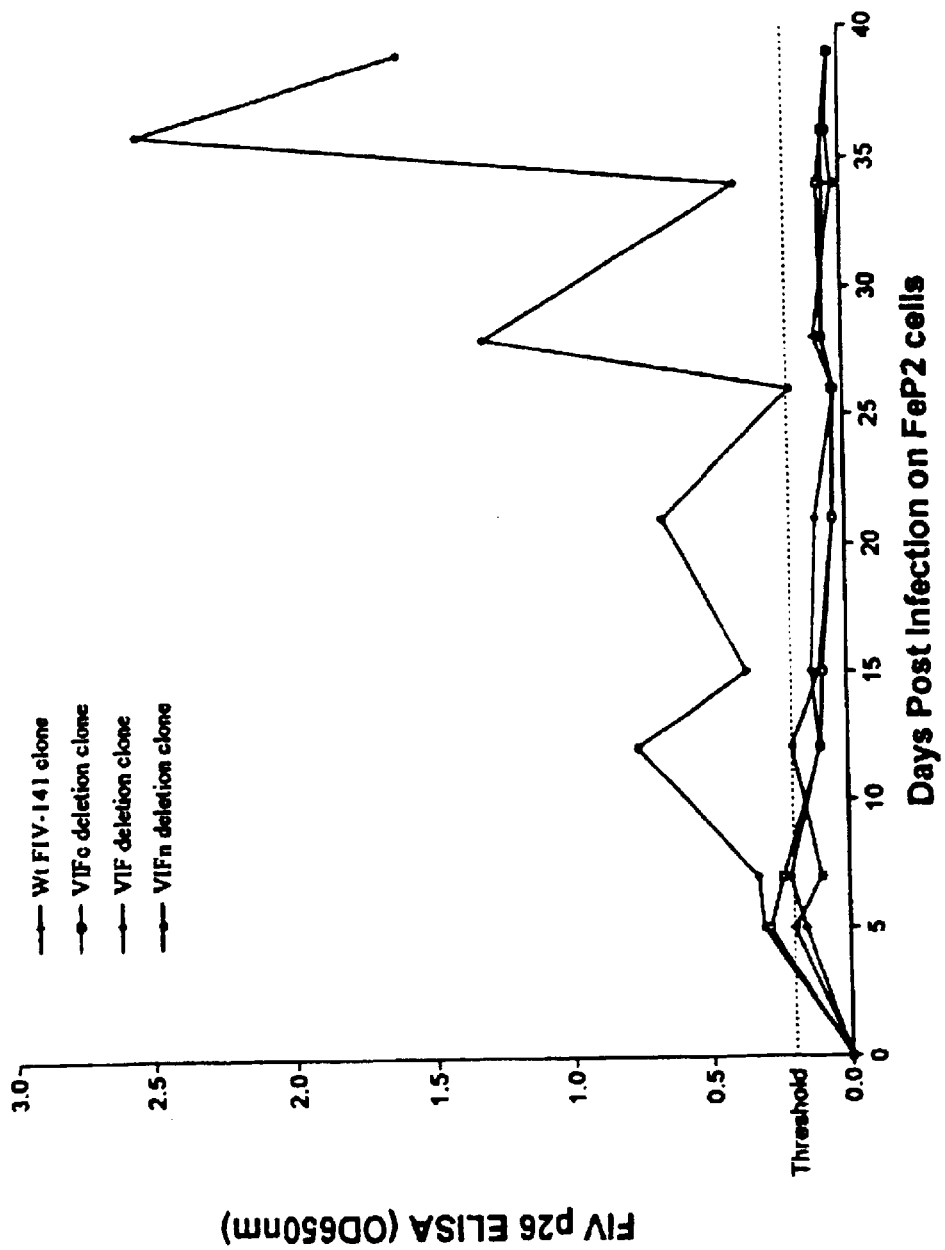
Figure 7:
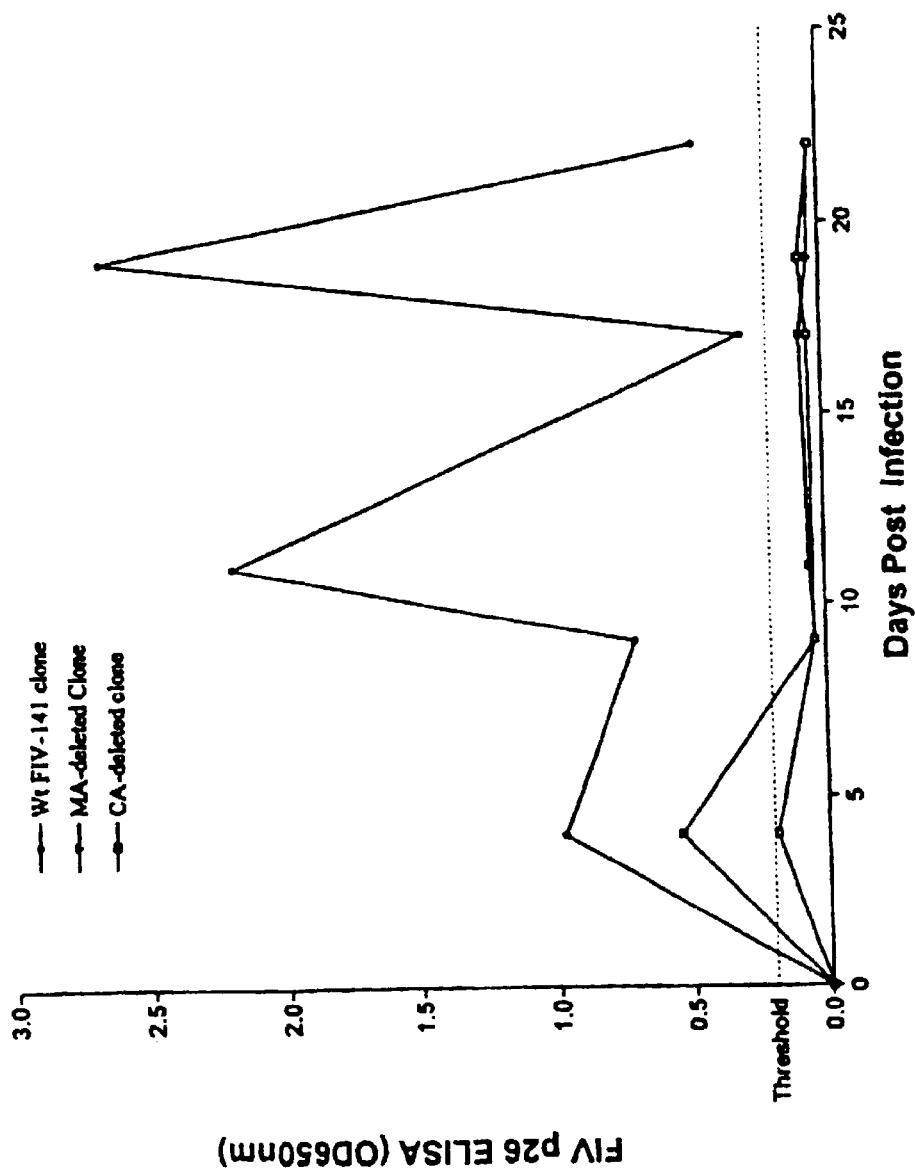
Figure 8:
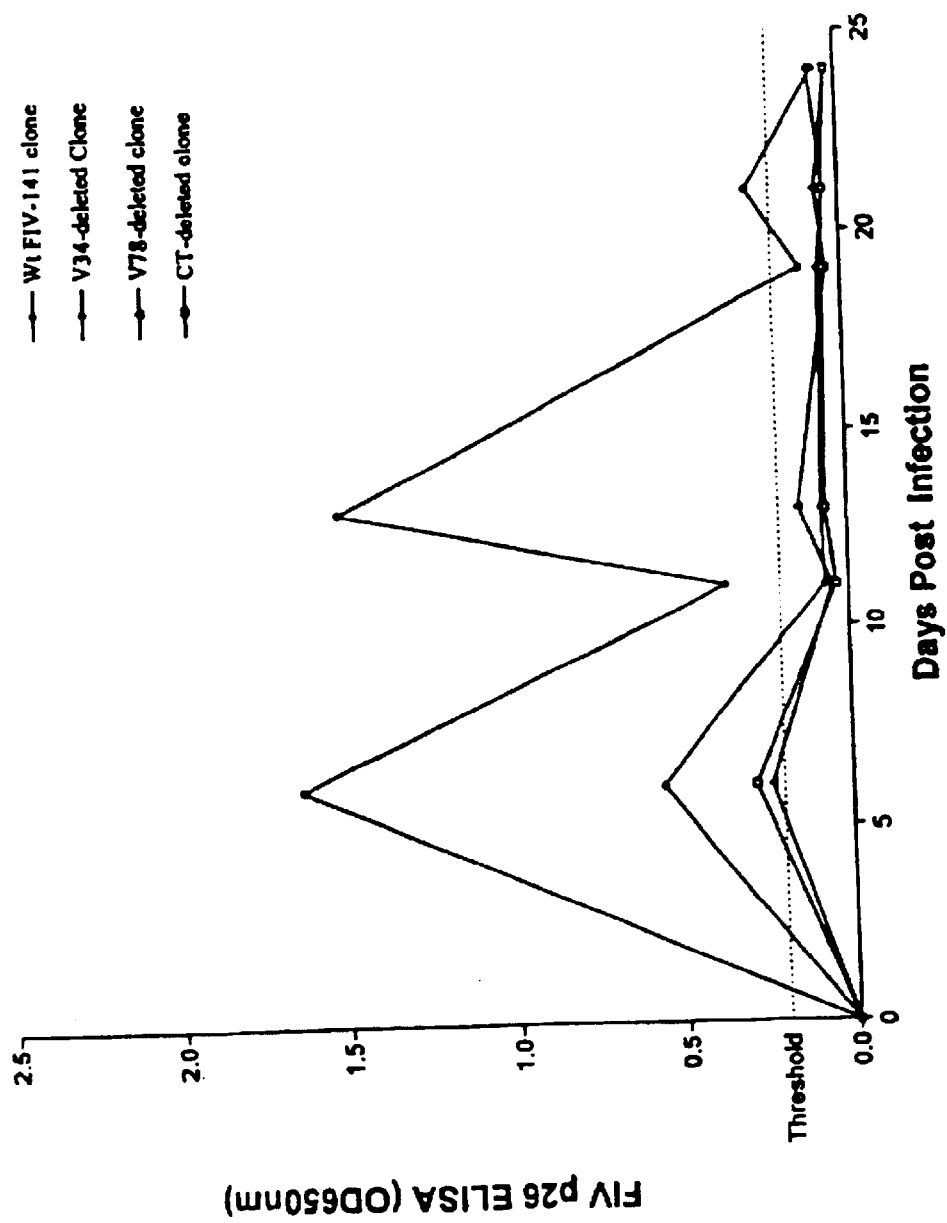
Figure 9:
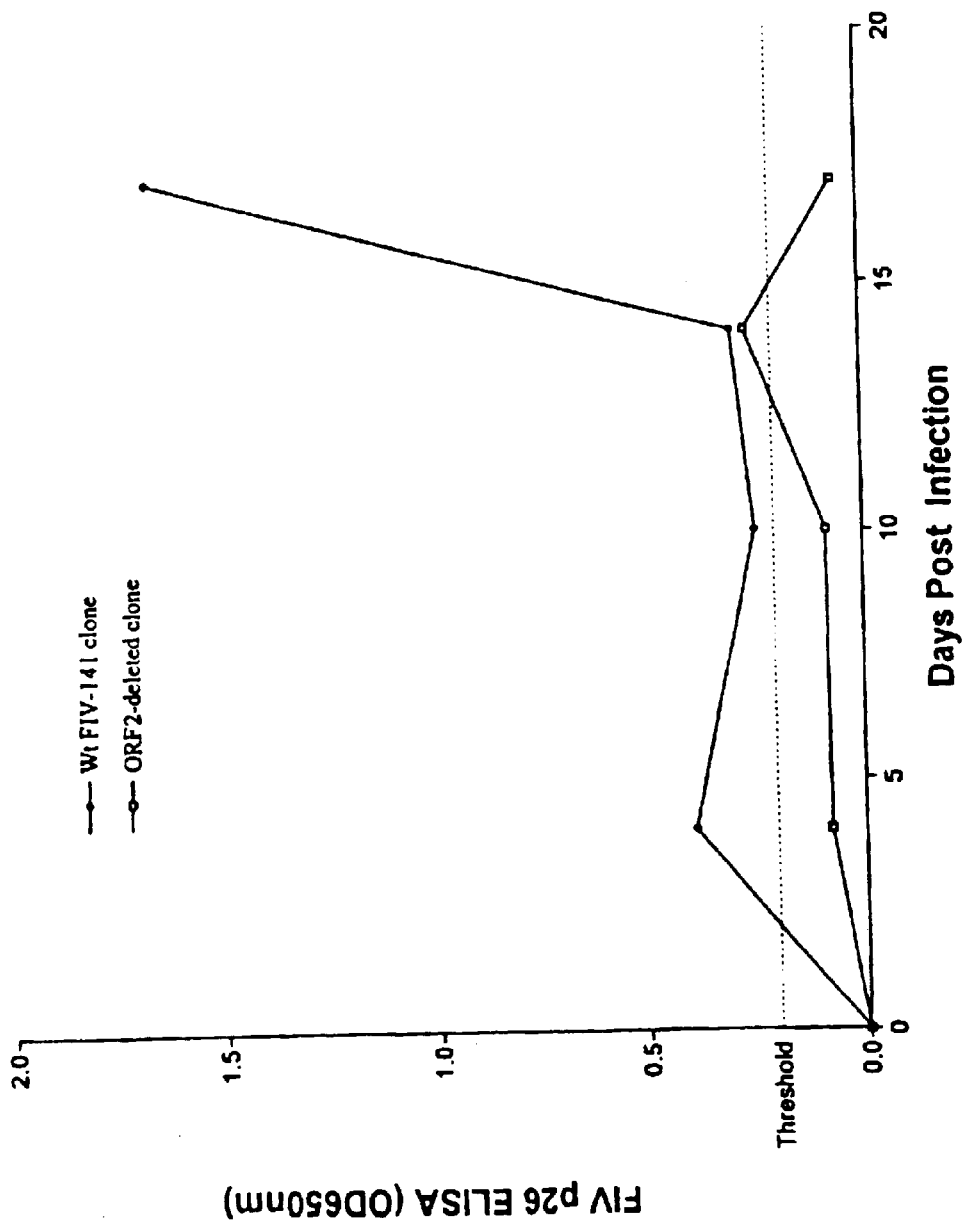
Figure 10:
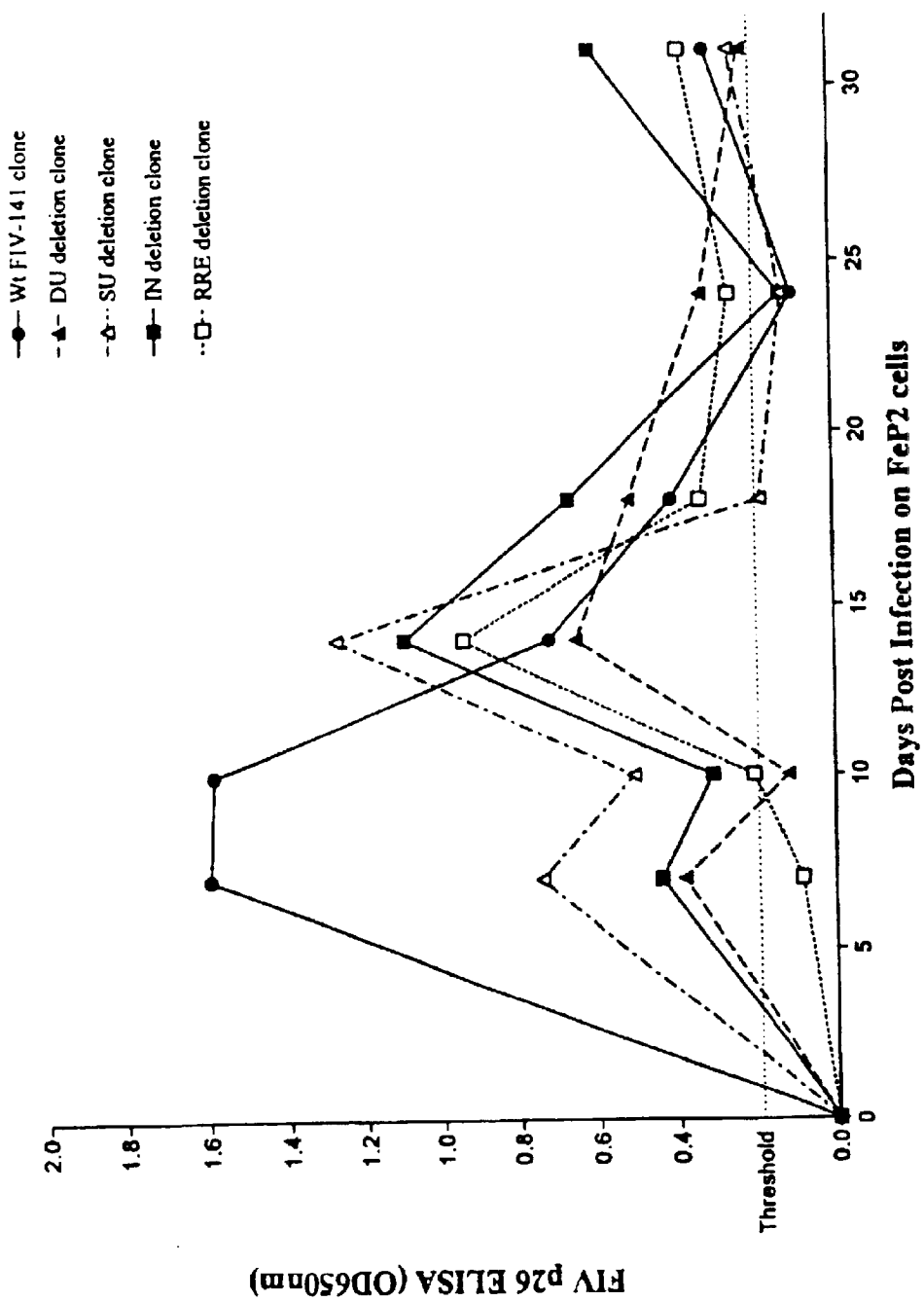

Twelve deletion clones were found to have no significant level of p26 capsid protein expression during the monitoring period. These included: ENV del; TMf del; and NC del (FIG. 5); 3 deletion clones from the Vif region (Vifn del; Vifc del; and Vif del) (FIG. 6); the MA and CA deletion clones (FIG. 7); the V3/4, V7/8 and CT deletion clones (FIG. 8); and the ORF(2) deletion clone (FIG. 9). The results indicate that deletions introduced into these clones totally abolish the infectivity of the virus in the FeP2 cells. Moderate levels of virus replication were detected for four deletion clones including DU del; SU del; IN del; and RRE del (FIG. 10).

E. Conclusions

ENV del

The ENV deletion clone, which has a deletion of 701 amino acids in the middle of the ENV protein (residues 106 to 806), totally lost the ability to infect FeP2 cells. Nevertheless, it maintained the ability to assemble and release defective virus particles, to encapsidate the viral genome, and to reverse transcribe RNA. The primary function of the ENV protein is to mediate virus entry into target cells during the early stage of infection. Deletion of the majority of the ENV protein may block virus entry and, hence, virus infectivity.

TMf del

The TMf deletion clone, containing a 25 amino acid deletion in the cleavage junction between the SU and TM proteins, is non-infectious in FeP2 cells. The deletion may block the cleavage processing of the ENV precursor protein, and this may result in a failure of viral particles to bind to and enter target cells. It has been reported that removal of the cleavage site of the ENV glycoprotein of FIV results in the expression of an uncleaved ENV precursor protein. However, the expressed recombinant protein maintains its antigenic properties, as evidenced by its interaction with monoclonal antibodies as determined using Western Blots and radioimmunoprecipitation assays (Rimmelzwaan et al., 1994, J. Gen. Virol. 75:2097–2012). Upon transfection into CRFK cells, the deletion clone produces defective virus particles at a level comparable to a wild type FIV-141 clone. The defective viral genome and RT enzymes were encapsidated in the defective virions.

SU del

SU del had a deletion of 503 amino acids from residue 106 to 608 of the SU protein. It was found to maintain levels of virus particle production approximately equal to that of the wild type clone. Both the gene-deleted viral genome and RT enzyme were encapsidated. However, in contrast to ENV del, cells transfected by SU del produced virus particles that are infectious in the FeP2 cells, although to a much lesser extent than the wild type virus. Thus, it appears that deletion of the SU protein from the FIV-141 genome attenuated the virus. It is believed that FIV binding to cellular receptors, which is the first step in virus infection, is mediated by the SU protein when associated with the TM protein. The mechanism by which the mutant virus binds to and enters target cells is unknown. An alternative pathway for the mutant virus to enter host cells may be responsible for the observed lower infectivity associated with the deletion clone.

V3/4 del and V7/8 del

One hundred forty-four amino acids from residues 360 to 503 of the SU protein (covering the V3 and V4 variable regions), and 72 amino acids from residues 98 to 169 of the TM protein (encompassing the V7 and V8 regions) were deleted in V3/4 del and V7/8 del respectively. Upon transfection into CRFK cells, each clone produced defective virus at levels similar to that observed for the wild type clone. As with other ENV-related deletion clones, V3/4 del and V7/8 del encapsidated their gene-deleted viral genomes and RT enzymes into virions. The infectivity assay indicated that deletion of the V3 and V4 region of SU, and deletion of the V7 and V8 region in the TM protein, totally abolished virus infectivity in the FeP2 cells. The V3 variable region is the immunodominant domain and has been reported to be involved in multiple functions, including virus tropism, viral pathogenesis, and neutralizing epitopes. It is not presently clear at which step viral infection was blocked in these two deletion clones.

CT del

The TM protein of FIV has a relatively long cytoplasmic tail (46 amino acids in length). Truncation of this tail in CT del clone resulted in a loss of infectivity of the virus in FeP2 cells. However, truncation had no effect on virus particle formation and encapsidation of the viral genome and RT protein. A specific functional interaction between MA and the TM cytoplasmic tail has been reported for FIV as well as for HIV-1. This interaction has been proposed to be important for the incorporation of the ENV protein into virions. Truncation of the cytoplasmic domain in CT del may eliminate the functional interaction between the MA and TM proteins, thereby blocking the incorporation of ENV.

MA del

MA del contains a 41 amino acid deletion from residues 85 to 125 at the C-terminus of the MA protein. Upon transfection into CRFK cells, the clone produced defective virus at a level comparable to that produced using the wild type FIV-141 clone. This indicates that deletion at the C-terminus domain has no significant effect on virus particle assembly and release. The gene-deleted viral genome and RT protein were encapsidated in the defective virus particles. When these virus particles were released from transfected CRFK cells, they were non-infectious with respect to FeP2 cells.

CA del

A deletion of 38 amino acids from residues 9 to 46 at the N-terminus of CA protein abolished viral particle formation, as evidenced by a negative signal in the p26 ELISA assay, the intra-virion RT PCR assay, and the RT activity assay. However, intracellular RT PCR from the transfected CRFK cells demonstrated that the deletion did not block viral RNA expression. Therefore, the failure to detect p26 protein or defective virus production in the supernatants of transfected cells is due to the block in viral particle assembly, not in viral protein expression.

NC del

The entire NC protein was deleted in the NC del clone. Cells transfected with this clone produced defective virus at a significantly reduced level compared to the wild type clone, indicating that deletion impaired viral particle assembly or release. It has been reported that the NC protein of HIV-1 is not required for the assembly of virus-like particles. The deletion in the NC clone did not effect the packaging of the RT enzyme into defective virions. As expected, no viral genome was encapsidated in the viral particles.

Vif del, Vifc del and Vifn del

Three deletion clones were constructed in the Vif gene, i.e., Vifn del, Vifc del, and Vif del. Vifn had a deletion of 50 amino acids at the N-terminal portion of the Vif protein. Vifc had a deletion of 146 amino acids at the C-terminal region of the protein, and Vif del had a deletion of almost the entire Vif protein. All three clones exhibited similar properties. Cells transfected with any of the three clones produced virus particles at a comparable rate to the wild type FIV-141 clone. Both viral genomes and RT enzyme were encapsidated in virions for all three clones. Virions released from CRFK cells transfected by the three clones were non-infectious with respect to FeP2 cells, indicating that Vif is required for virus replication in T lymphocytes.

ORF(2) del

The entire open reading frame of ORF(2) was deleted in the ORF(2) deletion clone. Cells transfected with the clone assembled and released viral particles at a comparable rate to the wild type clone. Although both viral genome and RT enzyme were packaged in the viral particles, the clone failed to replicate in FeP2 cells, suggesting that the gene product of ORF(2) is required for virus production in these cells.

RRE del

Eighty-four of the 150 total bases comprising the RRE sequence of FIV were deleted in RRE del. This deletion severely impaired viral structural protein expression and the production of viral particles in transfected cells. No p26 production in the supernatants of transfected CRFK cells was detected. Similarly, no packaged RT activity was measured. These results are in good agreement with the proposal that the RRE sequence is required for the export of unspliced and single-spliced viral RNA from the nucleus to the cytoplasm of cells. However, virion-associated viral genomic RNA was demonstrated to be present by RT PCR and the viral particles were infectious in FeP2 cells, although at a markedly reduced level compared with the wild type FIV-141 clone. Taken as a whole, these results indicate that deletion of the RRE sequence dramatically decreases the expression of viral structural proteins. However, it appears that the deletion did not totally abolish expression, and a trace amount of infectious virion particles was produced by the transfected cells.

IN del

Almost the entire IN protein was deleted in the IN del clone. Upon transfection into CRFK cells, the clone exhibited a level of viral protein expression and viral particle production comparable to that of the wild type clone. Virion-associated RT PCR and RT activity assays indicated that both viral genomic RNA and RT enzyme were packaged into viral particles. Surprisingly, the virions recovered from the cells transfected with the clone were infectious and could replicate in FeP2 cells, although at a reduced level compared with the wild type virus. Integration is an obligate step required for productive infection of a number of retroviruses, including HIV-1. The data suggest that the IN protein of FIV, in contrast to HIV, may not be an obligate requirement for viral protein expression and viral replication in FeP2 cells.

DU del

Almost the entire DU gene was deleted in the DU del clone. The product of this gene converts dUTP into dUMP. Deletion of the DU gene in the clone did not affect viral protein expression or viral particle production in transfected CRFK cells. Both viral genome and RT enzyme were encapsidated, and the virions produced from transfected cells were infectious for FeP2 cells. However, the deletion clone replicated in FeP2 at a slower rate than the wild type FIV-141 virus. This indicates that the DU gene is required for maximum replication of the virus. The data is consistent with reports that DU deleted FIV maintains its ability to propagate in T lymphocytes.

Example 5

Efficacy of Gene-Deleted FIV-141 Vaccines

Production of Gene-Deleted FIV-141 Plasmid DNA for Vaccination

Production of bulk purified plasmid DNA for vaccination was contracted to DNA Technologies, Inc., Gaithersburg, Md. Coded samples of each clone transformed into Stbl2 *E. coli* cells were sent to DNA Technologies, and each clone was grown in approximately 10 liters of LB medium. Supercoiled plasmid DNA was isolated by double CsCl density gradient centrifugation followed by extensive dialysis. The final purified DNA was dissolved in phosphate buffered saline (PBS) with 1 mM EDTA at a concentration of 2–5 μg/μl. Restriction digestion and endotoxin test were performed for each plasmid DNA preparation.

Vaccination and Challenge

Eleven experimental vaccines were prepared from plasmid DNA described above. The appropriate volume of stock DNA from each construct was dissolved in sterile PBS (GIBCO) to give 300 μg DNA in a 2 mL dose (Table 2). Placebo vaccine was also assembled using the pCR-Script SK(+) vector DNA.

Antibody-profile defined, barrier-reared domestic shorthair cats (approximately 8 weeks of age) were obtained from Liberty Research, Inc.(Waverly, N.Y.). The cats were vaccinated with killed vaccines to feline herpes virus, feline calicivirus, and feline parvovirus virus. Ten cats were randomly assigned by litter and sex to 13 groups prior to vaccination (Table 2).

TABLE 2

| Group | Vaccine | Vol/Dose | Challenge | Cat number |
|---|---|---|---|---|
| 1 | ENV del | 2 ml/300 μg | Yes | 10 |
| 2 | CA del | 2 ml/300 μg | Yes | 10 |
| 3 | Vif del | 2 ml/300 μg | Yes | 10 |
| 4 | IN del | 2 ml/300 μg | Yes | 10 |
| 5 | ORF(2) del | 2 ml/300 μg | Yes | 10 |
| 6 | MA del | 2 ml/300 μg | Yes | 10 |
| 7 | Tmf del | 2 ml/300 μg | Yes | 10 |
| 8 | V3/4 del | 2 ml/300 μg | Yes | 10 |
| 9 | V7/8 del | 2 ml/300 μg | Yes | 10 |
| 10 | MA del/Tmf del | 2 ml/300 μg | Yes | 10 |
| 11 | MA del/V3/4 del | 2 ml/300 μg | Yes | 10 |
| 12 | Placebo | 2 ml/300 μg | Yes | 10 |
| 13 | Placebo | 2 ml/300 μg | No | 10 |

Three vaccinations were administered at 4-week intervals when cats were 8, 12 and 16 weeks of age. Vaccines were administered into the quadriceps muscle (IM). Each 2 ml dose was divided equally between the muscles on the two hind legs. Four weeks following the last vaccination, all vaccine groups and one placebo group were challenged subcutaneously in the nape of the neck with FIV-141 virus at a dose of 354 $TCID_{50}$ when cats were 20 weeks of age. The second placebo vaccine group received a placebo challenge of Hank's balanced salt solution. Cats were observed for 12 weeks post-challenge.

Evaluation of Vaccine Efficacy

Similar to HIV-1 disease progression (Graziosi et al., 1993, Proc. Natl. Acad. Sci 90:6405–6409), FIV RNA load in plasma has been demonstrated to correlate with disease stage, and can predict disease progression in accelerated FIV infection (Diehl et al., 1995, J. Virol. 69:2328–2332; Diehl et al., 1996, J. Virol. 70:2503–2507). In this study, peripheral blood was drawn weekly for monitoring efficacy of the vaccination for 12 weeks post-challenge. Plasma viral loads were determined by quantitative competitive-reverse transcription-polymerase chain reaction (QcRT-PCR).

1. Quantitation of Viral RNA in Plasma by QcRT-PCR

Viral RNA was isolated from plasma samples using a QIAmp Viral RNA Purification Kit (Qiagen). Each purified RNA sample was distributed into four tubes, and into each tube was added an internal competitive RNA template with decreasing amounts of RNA (from 1000 fg, 100 fg, 10 fg to 1 fg). RNA samples were subjected to RT-PCR using a Titan One Tube RT-PCR System (Boehringer Mannheim). A one-step PCR protocol from the manufacturer was performed with minor modifications to increase the sensitivity of the assay. The RT-PCR reaction was set up in a total volume of 38.5 μl containing: 6.5 mM DTT, 0.3 units RNase inhibitor, 0.3 mM dATP, 0.3 mM dGTP, 0.3 mM dTTP, 0.3 mM dCTP, 10.4 ng of each FIV specific oligonucleotide, i.e., QPCR-11 (forward primer 1392-TGTAGAGCATGGTATCTTGAAGCATTAGGAAA-1423) (SEQ ID:58) and QPCR-O2 (reverse primer 2175-GTTCCTCTCTTTCCGCCTCCTACTCCAATCATATT-2141) (SEQ ID:59), 1.95 mM $MgCl_2$, and 1 ul of Titan Enzyme Mix. RT-PCR amplification conditions were 50° C. for 90 min; 94° C. for 3 min; followed by 30 cycles of denaturing at 94° C. for 30 sec, annealing at 55° C. for 1 min, and extension at 72° C. for 2 min; followed by 72° C. for 10 min.

Each PCR sample was separated on a 1.0% agarose gel and stained with ethidium bromide. Quantitation of viral RNA load was determined by comparing the intensity of the positive DNA band with that of the internal competitive standard control DNA band using the Gel-Doc system (Bio-Rad Laboratories).

2. Viral Load in Plasma Post-Challenge

Compared with the non-vaccinated (placebo) challenged group, cumulative viral RNA load in plasma was decreased in most of the vaccinated groups including those vaccinated with FIV-141 ENV del, CA del, V3/4 del, Vif del, MA del/Tmf del, MA del/V3/4 del, IN del and Tmf del vaccines (FIG. 11). The most significant decrease in plasma viral RNA load was achieved in group 1, which was vaccinated with FIV-141 ENV del vaccine. Group 1 exhibited a 10-fold decrease in cumulative plasma viral load over a period of 12 weeks post-challenge (FIG. 11). Following group 1 in response is group 2, which was vaccinated with FIV-141 CA del. An approximately 8-fold decease in plasma viral RNA load was observed in this group. Cats in groups 8, 10, 11 and 3 vaccinated with FIV-141 V3/4 del, MA del/Tmf del, MA del/V3/4 del and Vif del, respectively, showed a decrease of approximately 4-fold in plasma viral load. Cats in groups 4 and 7 vaccinated with FIV-141 IN del and Tmf del, respectively, exhibited a 2–3 fold decrease in plasma viral load. Viral RNA loads were slightly decreased in groups 5 and 9 vaccinated with FIV-141 ORF(2) del and V7/8 del vaccine, respectively. Vaccination enhancement of viral infectivity was observed in group 6, which was vaccinated with FIV-141 MA del, where the plasma viral load was increased about 50% over that of the non-vaccinated (placebo) challenged group. Thus, decreases in plasma viral load were demonstrated in several groups vaccinated with a vaccine of the present invention, especially the group vaccinated with FIV-141 ENV del vaccine.

Deposit of Biological Materials

The following biological materials were deposited with the American Type Culture Collection (ATCC) at 12301

Parklawn Drive, Rockville, Md., 20852, USA, on Jul. 1, 1998, and were assigned the following accession numbers:

|  | ATCC Accession No. |
| --- | --- |
| Viral strain FIV-141 | VR-2619 |
| Plasmid pFIV-141-B1 | 203001 |

All patents, patent applications, and publications cited above are incorporated herein by reference in their entirety.

The present invention is not to be limited in scope by the specific embodiments described, which are intended as single illustrations of individual aspects of the invention. Functionally equivalent compositions and methods are within the scope of the invention.

What is claimed is:

1. A method of making an attenuated FIV-141 virus that replicates upon entry into a host cell but which exhibits significantly reduced infectivity to feline T lymphocytes relative to the wild type FIV-141 virus, comprising mutating by deletion in an ENV gene of the wild-type virus.

2. A method of producing a mutated nucleic acid molecule suitable for use in a vaccine for FIV-141 virus infection, comprising
   a) reverse transcribing said FIV-141 virus's genomic RNA;
   b) cloning the reverse transcript of step (a) to form a cloned nucleic acid;
   c) mutating by deletion in the ENV gene of said cloned nucleic acid of step (b) to form a mutated nucleic acid molecule; and
   d) cloning said mutated nucleic acid of step (c).

3. The method of claim 2, wherein the mutated nucleic acid molecule encoding an attenuated FIV-141 virus, upon introduction into a host cell, produces an attenuated FIV-141 virus that replicates but which exhibits significantly reduced infectivity to feline T-lymphocytes relative to the wild-type FIV-141 virus.

* * * * *